US011214595B2

(12) United States Patent
Scott et al.

(10) Patent No.: US 11,214,595 B2
(45) Date of Patent: Jan. 4, 2022

(54) BK CHANNEL-MODULATING PEPTIDES AND THEIR USE

(71) Applicants: UNIVERSITY OF SOUTH FLORIDA, Tampa, FL (US); BOARD OF REGENTS, THE UNIVERSITY OF TEXAS SYSTEM, Austin, TX (US)

(72) Inventors: Luisa Lynn Scott, Austin, TX (US); Joseph Paul Walton, Tampa, FL (US)

(73) Assignees: UNIVERSITY OF SOUTH FLORIDA, Tampa, FL (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/222,534

(22) Filed: Dec. 17, 2018

(65) Prior Publication Data
US 2019/0112339 A1     Apr. 18, 2019

Related U.S. Application Data

(63) Continuation of application No. 15/650,375, filed on Jul. 14, 2017, now Pat. No. 10,183,972.

(60) Provisional application No. 62/362,316, filed on Jul. 14, 2016.

(51) Int. Cl.
| C07K 7/54 | (2006.01) |
| A61K 38/12 | (2006.01) |
| A61K 38/08 | (2019.01) |
| A61K 47/64 | (2017.01) |
| A61P 43/00 | (2006.01) |
| A61P 27/16 | (2006.01) |
| C07K 7/06 | (2006.01) |
| A61K 38/00 | (2006.01) |

(52) U.S. Cl.
CPC ............... *C07K 7/54* (2013.01); *C07K 7/06* (2013.01); *A61K 38/00* (2013.01); *A61K 38/08* (2013.01); *A61K 38/12* (2013.01); *A61K 47/64* (2017.08); *A61P 27/16* (2018.01); *A61P 43/00* (2018.01)

(58) Field of Classification Search
CPC ... C07K 7/06; C07K 7/54; C07K 7/64; A61K 38/00; A61K 38/08; A61K 38/12; A61K 47/64; A61P 27/16; A61P 43/00
See application file for complete search history.

(56) References Cited

FOREIGN PATENT DOCUMENTS

| WO | WO 00/50444 | 8/2000 |
| WO | WO 2011/102964 | 8/2011 |
| WO | WO 2012/098143 | 7/2012 |
| WO | WO 2015/120453 | 8/2015 |

OTHER PUBLICATIONS

Dobie, R.A. "Audiometric Threshold Shift Definitions: Simulations and Suggestions, Ear and Hearing" *Ear and Hearing*, Feb. 2005, 26(1):62-77.
Joo, S.H. "Cyclic Peptides as Therapeutic Agents and Biochemical Tools" *Biomolecules & Therapeutics*, 2012, 20(1):19-26.
Lee, U.S. et al. "BK Channel activation: structural and functional insights" *Trends in Neuroscience*, Sep. 2010, 33(9):415-423.
Scott, L.L. et al. "A novel BK channel-targeted peptide suppresses sound evoked activity in the mouse inferior colliculus" *Scientific Reports*, Feb. 14, 2017, 7:1-13.
Smith, G.R. et al. "Free energy of a potassium ion in a model of the channel formed by an amphipathic leucine-serine peptide" *European Biophysics Journal*, 2002, 31:198-206.
Scott, L.L. et al. "BK channel modulation of withdrawal from chronic ethanol exposure" poster presented at *C. elegans* Topic Meeting: Neuronal Development, Synaptic Function & Behavior (CeNeuro), Jul. 9, 2014, Madison, Wisconsin.
Mangieri, R.A. et al. "Novel BK-channel modulators alter ethanol-induced changes in excitability of accumbal D1R-expressing medium spiny neurons" poster presented at the 37th Annual Scientific Meeting of the Research Society on Alcoholism, Jun. 24, 2014, Bellevue, Washington.
Scott, L. et al. "A screen for peptides that alter BK channel-mediated alcohol behaviors" poster presented at the Society for Neuroscience Meeting, Nov. 11, 2013, San Diego, California.
Shen, A. et al. "Screening for drugs that reduce the symptoms of chronic ethanol withdrawal" poster presented at the Texas Research Society on Alcoholism, 23$^{rd}$ Annual Scientific Meeting, Feb. 22, 2013, Austin, Texas.
Scott, L. "Finding novel BK channel modulators that alter ethanol behaviors" poster presented at WCAAR Advance (UT Austin), 2014, Austin, TX.
Scott, L. et al. "Identifying Novel BK Channel Modulators" poster presented at the 19$^{th}$ International *C. elegans* meeting (sponsored by Genetics Society of America), Jun. 27, 2013, Los Angeles, California.
Zhi, M. et al. "Characterization of a Specific Phage-Displayed Peptide Binding to Vasculature of Human Gastric Cancer" *Cancer Biology & Therapy*, 2004, 3(12):1232-1235.
Petter, C. et al. "Phage Display Screening For Peptidic Chitinase Inhibitors" *J. Mol. Recognit.*, 2008, 21:401-409.
Frisina and Walton, Aging of the Mouse Central Auditory System, Handbook of Mouse Auditory Res: Behavior to Molecular Biology, edited by J. P. Willott (CRC Press, New York), 2001, Chap. 24, pp. 339-379.
Sha et al., Age-related auditory pathology in the CBA/J mouse, Hear Res. Sep. 2008; 243(1-2): 87-94.

(Continued)

*Primary Examiner* — Kimberly Ballard
(74) *Attorney, Agent, or Firm* — Quarles & Brady LLP

(57) ABSTRACT

The present invention concerns peptides and nucleic acids encoding the peptides, and their use for modulating large conductance $Ca^{2+}$ activated $K^+$ (BK) channel activity in cells; for treating conditions such as presbycusis (age-related hearing loss), audiogenic seizures, alcohol addiction, cancer, and neurodegenerative disease; and for delivering a cargo moiety to the brain of a subject through the blood-brain barrier.

10 Claims, 17 Drawing Sheets

Specification includes a Sequence Listing.

(56) References Cited

OTHER PUBLICATIONS

Ohlemiller and Frisina, Age-Related Hearing Loss and Its Cellular and Molecular Bases, 2008, Auditory Trauma, Protection, and Repair, Springer Handbook of Auditory Research, vol. 31., pp. 145-194.

Ohlemiller et al., Divergent Aging Characteristics in CBA/J and CBA/CaJ Mouse Cochleae, J Assoc Res Otolaryngol. Dec. 2010; 11(4): pp. 605-623.

Ison et al., Closing the Gap Between Neurobiology and Human Presbycusis: Behavioral and Evoked Potential Studies of Age-Related Hearing Loss in Animal Models and in Humans, Dec. 2009, The Aging Auditory System, Springer Handbook of Auditory Research 34, pp. 75-110.

Frisina, R. D. & Walton, J. P. Neuroanatomy of the central auditory system In Handbook of Mouse Auditory Research (ed. Willot, J.) 243-275 (CRC Press, 2001).

30 million peptide sequences

Enriched fraction: 26 unique sequences

Peptide synthesis: 20 sequences

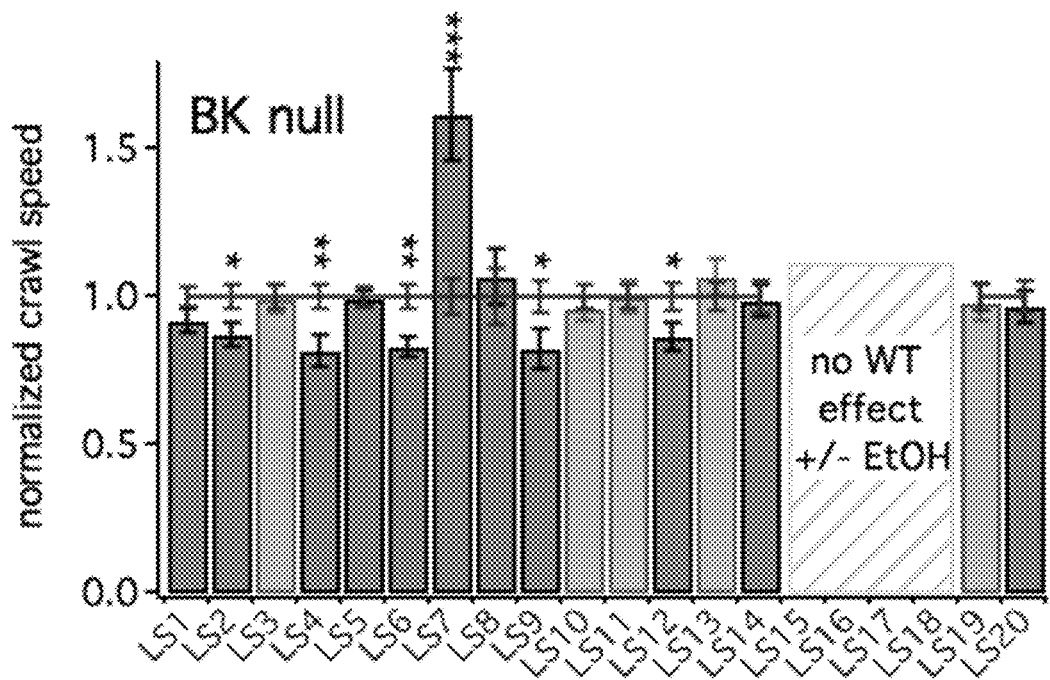
FIG. 3D
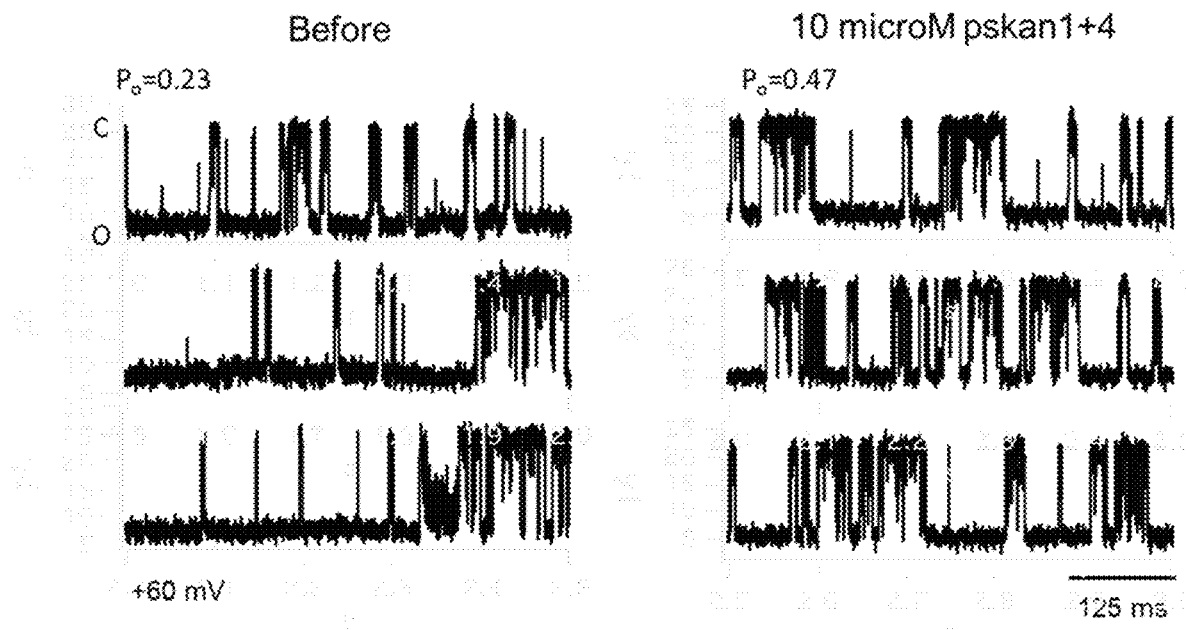
FIG. 4A
FIG. 4B

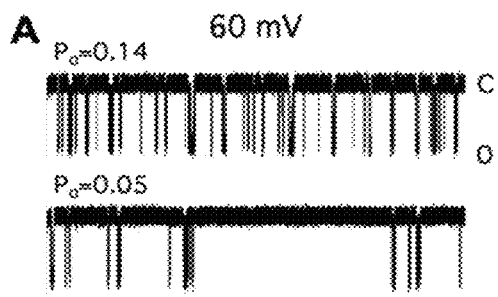 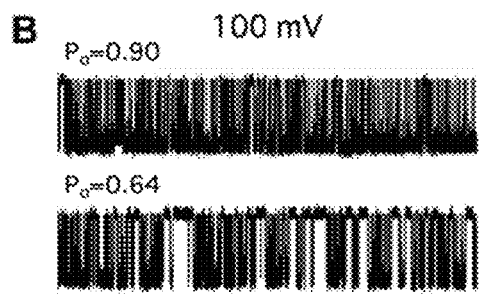
FIG. 6A  FIG. 6B
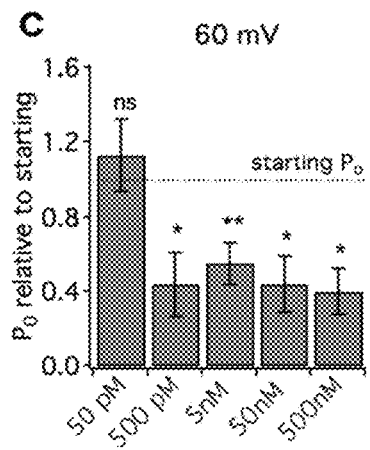 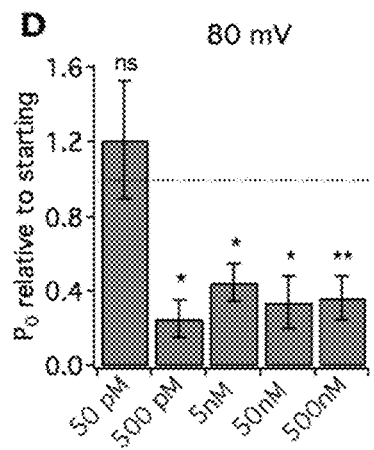 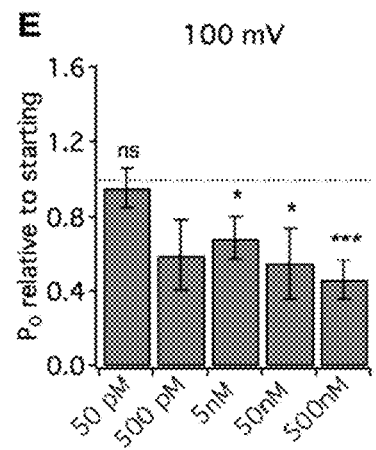
FIG. 6C  FIG. 6D  FIG. 6E
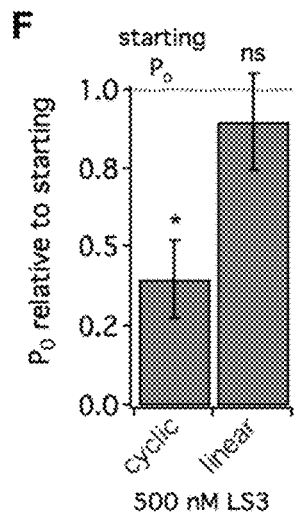 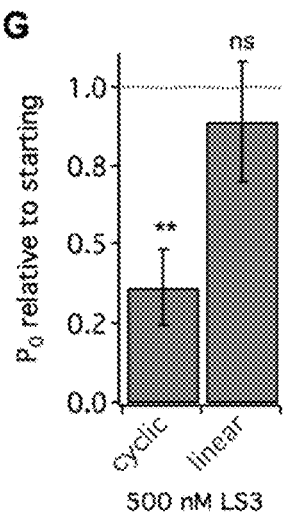 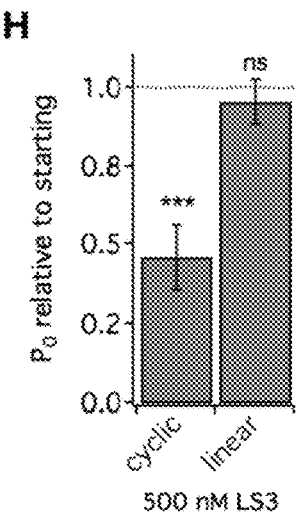
FIG. 6F  FIG. 6G  FIG. 6H

FIG. 9A    FIG. 9B    FIG. 9C

BK CHANNEL-MODULATING PEPTIDES AND THEIR USE

CROSS-REFERENCE TO RELATED APPLICATION

The present application is a continuation of U.S. application Ser. No. 15/650,375, filed Jul. 14, 2017, which claims the benefit of U.S. Provisional Application Ser. No. 62/362,316, filed Jul. 14, 2016, which is hereby incorporated by reference herein in its entirety, including any figures, tables, nucleic acid sequences, amino acid sequences, or drawings.

GOVERNMENT SUPPORT

This invention was made with government support under Grant No. AA0202992 awarded by the National Institutes of Health. The government has certain rights in the invention.

BACKGROUND OF THE INVENTION

Large conductance calcium activated channels are broadly expressed in neurons and muscle where they modulate cellular activity and function. Decades of research support an ongoing interest in modulating large conductance $Ca^{2+}$ activated $K^+$ (BK) channel function to alter disease states.

Age-related hearing loss (ARHL) is a widespread medical problem affecting approximately 30-40% of people 65 and older, while >50% of people 75 and older have difficulty hearing. The primary etiology of ARHL is two-fold, i) a loss in sensitivity to sound resulting from functional deficits in inner ear transduction and ii) alteration in central auditory processing within the brain. Deficits at the inner ear raise the threshold for how a loud a sound must be to be heard, particularly for higher pitched sounds. Many consonances are high-pitched sounds, making this deficit directly interfere with one's ability to understand speech. These types of hearing deficits can be improved with current hearing aid technology, although some patients may resist wearing hearing aids. Much more difficult to improve with hearing aids is the functional loss in the brain's ability to process sounds. These central auditory processing deficits make it very difficult to understand speech in a noisy environment.

The large conductance calcium-activated potassium (BK) channel is a promising pharmacological target. Widely expressed in human tissue where it is gated by voltage and intracellular calcium, the BK channel regulates smooth muscle tone, endocrine secretion and neuronal excitability. Despite broad expression, global knockout of the constitutive pore-forming a subunit is not lethal in mice. In *Caenorhabditis elegans* and *Drosophila*, null mutations in the highly conserved invertebrate BKα channel reduces acute ethanol intoxication and tolerance.

Restriction of BK channel function has therapeutic value in human disease. Human tumor growth and metastasis is supported by higher BK channel expression and curtailed by BK channel blockers. In the CNS, a BK channel gain-of-function mutation is associated with an increased risk for epilepsy in humans and mice, and blocking BK channel function suppresses seizure activity in vivo and in vitro. BK channels are expressed throughout the auditory system where they maintain high frequency firing. Thus, suppression of BK channel function in the inferior colliculus (IC) may restrict audiogenic seizures, which originate in this region. A reduction in high frequency firing in the IC could also reduce tinnitus or "ringing in the ears." Evidence from animal models of tinnitus suggests that a focal loss of output from the cochlea, common in many cases of tinnitus, in turn suppresses inhibitory drive in the central auditory system resulting in hyperexcitability. This neuronal hyperexcitability is evident in both the cochlear nucleus and at the level of the IC.

A number of peptides alter BK channel function. Peptide scorpio- or conotoxins block the pore with low nanomolar affinity and high specificity but have relatively complex structures restricting large-scale synthesis. Small, endogenous peptides or peptide fragments modulate BK channel function, but mainly act with lower affinity. For example, fragments of a BK channel auxiliary subunit (β2) inactivate currents in the micromolar range. There are currently no BK channel-directed peptides for CNS pharmacological applications, having high affinity and specificity, blood-brain barrier (BBB) permeability and amenability to large-scale synthesis.

BRIEF SUMMARY OF THE INVENTION

The present convention concerns peptides that modulate large conductance $Ca^{2+}$ activated $K^+$ (BK) channel activity, compositions containing the peptides, and methods of using the peptides and compositions for the treatment and prevention of diseases and disorders. In some embodiments, the peptide is one listed in Table 1 or a functional fragment or variant thereof. The peptide may be a linear peptide or a cyclic (non-linear) peptide.

In some embodiments, the peptide is LS3 (CRRGLVQVC (SEQ ID NO:3)). This peptide suppresses channel gating of heterologously expressed human BK channels in the high picomolar range. In vivo experiments in wild type or BK channel-humanized *Caenorhabditis elegans* show that LS3 suppresses locomotor activity via a BK channel-specific mechanism.

The peptide can shuttle both itself and small molecule cargo across the blood-brain barrier of the mammalian brain. When tagged with fluorescein and topically applied to the dural surface of the auditory midbrain, the peptide traveled to a depth of at least 1200 microns into the inferior colliculus. Once across the blood-brain barrier, the peptide shows a concentration-dependent effect on sound-evoked activity in inferior colliculus neurons. Topical application of ~0.8 mgs/kg LS3 on the dural surface of the mouse auditory midbrain suppressed sound evoked neural activity, similar to a general pore blocker, in vivo, which recovered after 24 hours. Similar action on sound-evoked activity was seen when injected systemically (i.p. at ~0.4 mgs/kg), except that the effects took longer to be observed. When administered at a ten-fold lower dose, the peptide lowered sound-evoked thresholds and provided better definition to neuronal receptive fields in aged mice. Together these data show that a novel BK channel-directed peptide potently and specifically alters channel gating and crosses the blood-brain barrier to modulate neural activity in vivo. High dose application supports these peptides' use for suppressing audiogenic seizures, while the lower dose supports these peptides' use for reducing the effects of age-related hearing loss.

One aspect of the invention concerns a peptide comprising an amino acid sequence of Table 1, i.e., selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26), or a functional fragment or variant of any one of the foregoing amino acid sequences. In some embodiments, the peptide is a circular peptide. In some embodiments, the peptide has an N-terminal and C-terminal disulfide bridge (i.e., a disulfide bridge between the cysteines).

In some embodiments, the peptide comprises an amino acid sequence selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26). In some embodiments, the peptide is a circular peptide. In some embodiments, the peptide has an N-terminal and C-terminal disulfide bridge (i.e., a disulfide bridge between the cysteines).

In some embodiments, the peptide consists of an amino acid sequence selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26). In some embodiments, the peptide is a circular peptide. In some embodiments, the peptide has an N-terminal and C-terminal disulfide bridge (i.e., a disulfide bridge between the cysteines).

In some embodiments, the peptide comprises CRRGLVQVC (SEQ ID NO:3). In some embodiments, the peptide comprises an amino acid sequence consisting of CRRGLVQVC (SEQ ID NO:3), including no further amino acid residues. In some embodiments, the peptide consists of CRRGLVQVC (SEQ ID NO:3). In some embodiments, the peptide is a circular peptide. In some embodiments, the peptide has an N-terminal and C-terminal disulfide bridge (i.e., a disulfide bridge between the cysteines).

In some embodiments, the functional fragment or variant is a peptide comprising an amino acid sequence comprising any one of SEQ ID NO:27-61. In some embodiments, the functional fragment or variant is a peptide comprising an amino acid sequence consisting of any one of SEQ ID NO:27-61 (including no further amino acid residues). In some embodiments, the functional fragment or variant is a peptide consisting of an amino acid sequence consisting of any one of SEQ ID NO:27-61. In some embodiments, the peptide is a circular peptide. In some embodiments, the peptide has an N-terminal and C-terminal disulfide bridge (i.e., a disulfide bridge between the cysteines).

Optionally, the peptide of the invention may have a heterologous amino acid sequence or a moiety fused directly or indirectly to the peptide of the invention, which is then referred to as a polypeptide construct. In some embodiments, the heterologous moiety comprises a label that is detectable using an appropriate detection modality In some embodiments, the polypeptide construct is a fusion polypeptide comprising a first amino acid sequence of the invention and a second amino acid sequence fused directly or indirectly to the first amino acid sequence. Thus, in some embodiments, the fusion polypeptide comprises a first amino acid sequence of the invention, e.g., an amino acid sequence selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26), or an amino acid sequence having one or more conservative substitutions or deletions of any one of the foregoing, and a second amino acid sequence fused directly or indirectly to the first amino acid sequence. The second amino acid sequence may be fused to the amino-terminus (N-terminus) or carboxyl-terminus (C-terminus) of the first amino acid sequence. The fusion may be direct or indirect through a linker. The first amino acid sequence may be identical to or different from the second amino acid sequence. The fusion polypeptide may further comprise one or more additional amino acid sequences directly or indirectly fused to the first amino acid sequence or second amino acid sequence, making a "multimer".

Another aspect of the invention concerns a nucleic acid encoding any of the aforementioned peptides of the invention. Another aspect of the invention concerns an expression construct, such as a viral or non-viral vector, comprising the nucleic acid encoding any of the aforementioned peptides of the invention.

Another aspect of the invention concerns a composition comprising a peptide of the invention, a nucleic acid encoding the peptide, or an expression construct comprising the nucleic acid; and a pharmaceutically acceptable carrier or diluent.

Another aspect of the invention concerns a method for treating a condition in a subject in need thereof, comprising administering an agent of the invention to the subject, wherein the condition is selected from among presbycusis, audiogenic seizures, alcohol addiction, cancer, and neurodegenerative disease (e.g., Alzheimer's disease (AD), Parkinson's disease (PD), Huntington's disease). The agent may be a peptide of the invention, a nucleic acid encoding the peptide, an expression construct comprising a nucleic acid encoding the peptide. The agent may be administered to the subject in a composition comprising the agent and a pharmaceutically acceptable carrier or diluent.

The agent may be administered to the subject by any route effective in delivering the agent to the desired anatomical location or locations. In some embodiments, the agent is administered systemically. In some embodiments, the agent is administered locally. In some embodiments, the agent is administered to the subject by a route selected from the group consisting of intravascular (e.g., intravenous or intraarterial), intramuscular, intracutaneous, oral, intranasal, intra-ocular, topical, and transdermal.

The agent may be administered to the subject as therapy or prophylaxis. Thus, in some embodiments, the subject has the condition at the time the agent is administered, and the agent is administered to the subject as therapy for the condition. In other embodiments, the subject does not have the condition at the time the agent is administered, and the agent is administered to prevent or delay the onset of the condition.

Optionally, one or more additional biologically active agents are administered to the subject before, during, or after administration of the agent. For example, the one or more additional agents may have activity that is useful in treating or delaying onset of the condition. The one or more additional biologically active agents may be administered within the same composition as the agent or in separate composition. Thus, the composition may include one or more additional biologically active agents.

In some embodiments, the agent comprises a peptide comprising or consisting of an amino acid sequence of Table 1. In some embodiments, the agent comprises a peptide comprising CRRGLVQVC (SEQ ID NO:3). In some embodiments, the agent comprises a peptide comprising an amino acid sequence consisting of CRRGLVQVC (SEQ ID NO:3).

Another aspect of the invention concerns a method for modulating large conductance $Ca^{2+}$ activated $K^+$ (BK) channel activity in a cell having a BK channel in vitro or in vivo, comprising contacting the cell in vitro or in vivo with an agent of the invention. In some embodiments, the BK channel activity is BKα channel function. The agent may be a peptide of the invention, a nucleic acid encoding the peptide, or an expression construct comprising a nucleic acid encoding the peptide, wherein the condition is selected from among presbycusis, audiogenic seizures, alcohol addiction, cancer, and neurodegenerative disease. The agent may be contacted to the cell in a composition comprising the agent and a pharmaceutically acceptable carrier or diluent. As used herein, the term "contacting" in this context means bringing the agent into contact with the cell, or vice-versa, or any other manner of causing the agent and the cell to come into contact.

In some embodiments, the agent comprises a peptide comprising or consisting of an amino acid sequence of Table 1. In some embodiments, the agent comprises a peptide comprising CRRGLVQVC (SEQ ID NO:3). In some embodiments, the agent comprises a peptide comprising an amino acid sequence consisting of CRRGLVQVC (SEQ ID NO:3).

In the BK modulation method, the BK channel may be native to the cell or the BK channel may be heterologous to the cell. For example, the cell can be genetically modified to transiently or stably express a nucleic acid encoding a BK channel that is heterologous to the cell. In some embodiments, the cell is a human cell. In other embodiments, the cell is a non-human animal cell.

Another aspect of the invention concerns a method of delivering a cargo moiety to the brain of a subject, through the blood-brain barrier (BBB), comprising administering a polypeptide construct to the subject, wherein the polypeptide construct comprises a peptide of the invention conjugated to the cargo moiety.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 2B depicts a sequence logo showing the relative likelihood of amino acid expression for all twenty candidate peptides selected by the phagemid display screen (see SEQ ID NO:1-20 of Table 1). Only the amino acid positions that were randomized in the phagemid display library (amino acids 2-7) are shown. Charged amino acids, particularly arginine (R), were highly enriched at all positions followed by small amino acids like glycine and alanine. Two or more amino acids in a fixed position or three or more amino acids in a sliding position (*) that were shared across two or more peptides were considered motifs. Motifs are color coded by fold enrichment over theoretical frequency in the original phagemid display library.

FIGS. 3A-3D. Candidate peptides showed selective BK channel functional activity in C. elegans. To assess the functional activity of the peptides, worms were incubated with 750 µM peptide or vehicle (NGM) for 30 minutes. Post-incubation crawl speed was measured before and after a 20-minute exposure to ethanol. For all trials, peptide- and vehicle-treated worms were run in tandem. Crawl speeds were normalized to the vehicle-treated controls in each trial. Means±SEM are shown as bars (gray or turquoise) for the peptide-treated groups and as lines for the vehicle-treated groups (maroon). Half of the peptides caused strongly significant (*p<0.001) changes in crawl speed for WT (N2) worms before (FIG. 3A) and/or after ethanol exposure (FIG. 3B). LS15-18 showed no significant effect and were eliminated from the screen. All other peptides were tested for effects on a strain (NM1968) expressing a null allele of the worm BK channel ortholog, slo-1. Of those that effected WT crawl speed, only five peptides showed no effect both before (FIG. 3C) and after ethanol exposure (FIG. 3D). All peptides were tested on at least 2 days and 30 worms. For peptides exhibiting selective BK channel functional activity (turquoise), all peptides were tested on at least 3 days and 60 worms. Student's t-tests compared the peptide-treated vs. vehicle-treated worms run in tandem; *p<0.001, **p<0.01, *p<0.05.

FIGS. 4A-4B. BK channel-targeted peptides act as openers on human BKα channels. FIGS. 4A and 4B: Pskan 1+4. Electrophysiological recordings of human BKα channels expressed in HEK293 cells showed that the combination of pskan1 and pskan4 increases channel opening. When a 10 microM peptide solution was applied to outside-out patches held at +40 to +60 mV and 700 nM to 1 µM intracellular Ca2+, the probability of opening increased 1.6±0.22 fold (n=7).

FIG. 5C shows schematics representing the enriched amino acid motifs in the four select peptides. Each motif is represented by a unique color. Dual coloring indicates the residue is shared between motifs. LS19 and LS11 shared a motif, while the others expressed unique motifs.

FIGS. 6A-6H. LS3 alters the gating of human BK channels. Human BKα channels (ZERO isoform) expressed in HEK293 cells were recorded in inside-out patches. Peptide was applied by diffusion to the extracellular side. Intracellular calcium held at 750 nM. FIGS. 6A, 6B, Single channel traces show 500 nM LS3 reduces the probability of opening at 60 mV (FIG. 6A) and 100 mV (FIG. 6B). FIGS. 6C-6E, Bar graphs displaying the post-peptide $P_o$ relative to the starting $P_o$ across LS3 concentrations. At 500 pM through 500 nM LS3 reduced the $P_o$ at each holding potential (pre vs. post: *p<0.05, p<0.01, *p<0.001, N=6-12, planned Student's t-tests). 50 pM LS3 did not significantly alter the $P_o$. FIG. 6F-6H, Bar graphs displaying the post-peptide $P_o$ relative to the starting $P_o$ for either 500 nM LS3 (cyclic) or 500 nM of the reduced form of LS3 (linear). Unlike LS3, the linear form did not alter $P_o$ (N=6-12, planned Student's t-tests).

FIGS. 7A-7C, Bar graphs showing one example of changes in open and closed dwell times before (red) and after (black) 500 nM LS3 (100 mV). Channel open dwell times shortened (FIG. 7A). Three-component exponential fits of closed dwell times (FIG. 7B) showed that the longest duration dwell times (component 2) lengthened while short dwell times (component 0) did not change significantly. FIG. 7C, Bar graph (right) of the change in mean open times (left) at each holding voltage shows that LS3 shortened openings (pre vs. post mean open times: *p<0.05; N=8, planned Student's t-tests). Bar graph (left) of the change in peak times for short (black) and long (gray) duration closings shows that only the longest duration closings lengthened (pre vs. post peak times: *p<0.05, **p<0.01; N=8, planned Student's t-tests).

FIG. 8D shows that after 3 hours, driven activity fell from 430 to 130 spikes, ~70% reduction (N=5 mice). Similarly, application of the pore blocker paxilline (1 µL of 10 µM stock) to the surface of the IC (N=5 mice) resulted in an 87% reduction in sound driven activity 5 hours post-application (FIGS. 8B and 8E). FIGS. 8C and 8F show the effects of a systemic injection (0.3 mg/kg I.P.) of LS3. A steady decline in sound evoked activity was observed over 2 hours, which accounted for an 85% reduction in spikes within the RF (N=5 mice).

FIGS. 9A-9D. LS3 alters BK channel function in wild type or humanized C. elegans. FIGS. 9A-9C, Bar graphs of crawl speeds for vehicle- (gray) and LS3-(red) treated groups show that LS3 reduced crawl speed for wild type but not slo-1(null) worms at 75 µM (FIG. 9A), 250 µM (FIG. 9B) and 750 µM (FIG. 9C; LS3 vs. vehicle for all concentrations: *p<0.001, N=81-210, planned Student's t-tests). FIG. 9D, Bar graph of crawl speeds shows that a reduction in crawl speed by 750 µM LS3 was rescued on the slo-1 null background with extrachromosomal expression of either the worm (slo-1(+)) or the human (hslo(+)) BK channel gene (LS3 vs. vehicle: *p<0.001, N=78-162, planned Student's t-tests).

FIGS. 12A, 12B-1, 12B-2, 12C, 12D, and 12E. LS10 substantially reduces the probability of opening of the worm BK channel but not the human BK channel. FIG. 12A shows the structure of LS10. FIGS. 12B-1 and 12B-2: representative three second traces at 100 mV before and after LS10 (500 nM). Both the ZERO (FIG. 12B-1) and STREX (FIG. 12B-2) isoforms of the human BKα channel showed little change in the probability of opening ($P_o$). BKα channels expressed in HEK293 cells were recorded in inside-out patches. Intracellular calcium held at 750 nM. FIG. 12C shows the mean fold change in $P_o$ in response to 500 nM LS10 for the ZERO (open bars) and STREX (shaded bars) isoforms of the human BKα channel. FIG. 12D shows representative three second traces at 100 mV before and after LS10 (500 nM). The worm BK channel (SLO-1) showed a significant reduction in the probability of opening ($P_o$). SLO-1 channels expressed in oocytes cells were recorded in inside-out patches. Intracellular calcium held at 5 μM. FIG. 12E shows the mean fold change in $P_o$ in response to 500 nM LS10 for the SLO-1 channel.

FIGS. 13A-1, 13A-2, 13B, 13C-1, 13C-2, 13D-1, and 13D-2. LS10 shortens open dwell times of the human BK channel. Single human BKα (ZERO isoform) channels expressed in HEK293 cells were recorded in inside-out patches before and after 500 nM LS10. Intracellular calcium held at 750 nM. FIGS. 13A-1 and 13A-2: open dwell times before (FIG. 13A-1) and after (FIG. 13A-2) LS10 for a representative recording at 100 mV. Single exponential fit, red line. FIG. 13B: the mean change in peak open dwell times in response to LS10. Paired Student's t-tests compared the pre- and post-peptide peak open durations, *$p<0.05$, N=5-6). FIGS. 13C-1 and 13C-2: closed dwell times before (FIG. 13C-1) and after (FIG. 13C-2) LS10 for a representative recording at 100 mV. Half of the recordings showed a lengthening in closed times like this one. Three component exponential fits (gray dotted-lines) and summation (red lines) also indicated. FIGS. 13D-1 and 13D-2: the mean change in peak short (FIG. 13D-1) and long (FIG. 13D-2) duration closed dwell times in response to LS10. Paired Student's t-tests compared the pre- and post-peptide peak open durations, *$p<0.05$, N=6.

FIGS. 14A-1, 14A-2, and 14B. LS10 prevents the potentiation of BK channels by acute ethanol exposure. SLO-1 channels expressed in oocytes cells were recorded in inside-out patches before. Intracellular calcium held at 5 μM. FIGS. 14A-1 and 14A-2: representative three second traces at 100 mV before (upper traces) and after (lower traces) bath application of 50 mM ethanol. Control (FIG. 14A-1) recording shows normal potentiation of the probability of opening ($P_o$) by ethanol, which is blocked in the presence of 500 nM LS10 (FIG. 14A-2). FIG. 14B: mean $P_o$ change in response to ethanol for control recordings (open bars) and in the presence of LS10 (shaded bars). Paired Student's t-tests compared the $P_o$ before and after ethanol, *$p<0.05$, N=5.

BRIEF DESCRIPTION OF THE SEQUENCES

Figure 1:
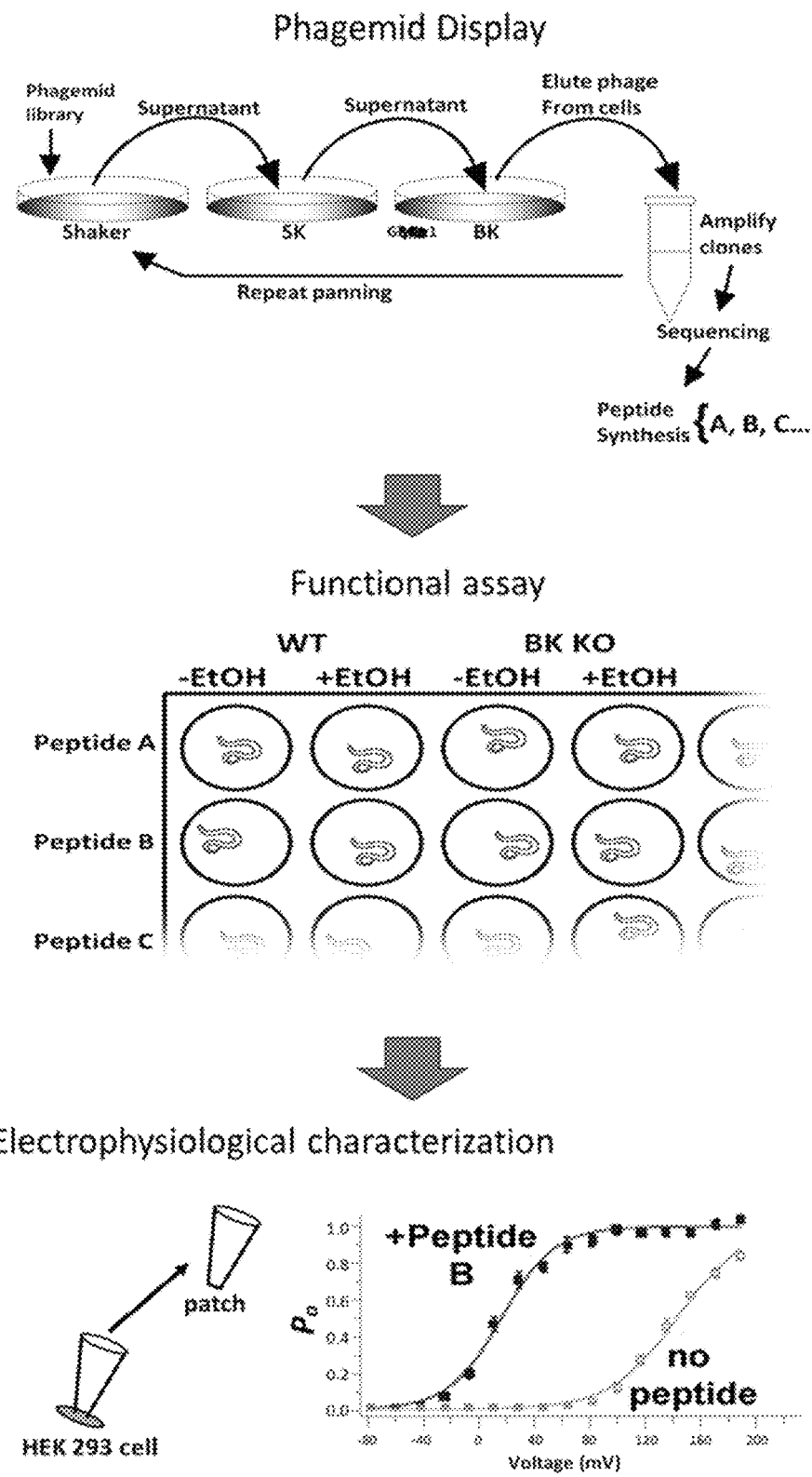
FIG. 1. Strategy to identify peptides that affect ethanol modulation of human BK channel function. Phage display was used to identify peptides that bind to the human BK channel. Modified bacteriophage (phagemid), each expressing one of a randomized library of small peptides, were serially panned against ion channels expressed in HEK 293 cells. Phagemid that did not bind to hGlyRa1 or rSK2 channels but did bind to the human BKα channel were collected, amplified and re-panned for a total of 5 times. Phagemid were sequenced and the peptide sequences synthesized. Peptides were screened for their ability to affect BK channel function using C. elegans. In C. elegans, locomotion and ethanol-induced locomotor suppression are BK channel-mediated processes. To test peptide function, locomotor ability with and without peptide were compared between wild-type and BK null animals in the presence and absence of ethanol (EtOH). For peptides suspected of modulating BK channel function, effects on channel gating were characterized using electrophysiological methods. Macro and single channel currents were recorded in patches pulled from HEK 293 cells expressing human SLO channels in the presence and absence of peptide and ethanol.
Figure 2A:
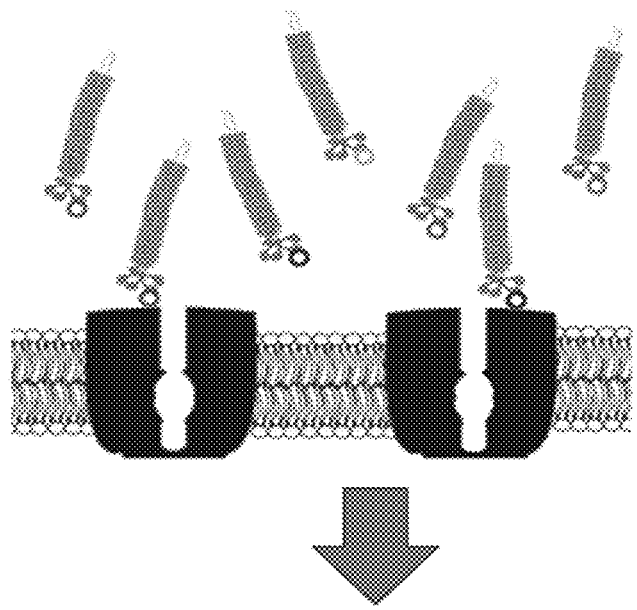
FIGS. 2A-2B. Phagemid display selection of peptides that bind to the human BKα channel. 3 motifs were enriched 3000-6000 fold (p<0.0001). Positively charged amino acid clusters were enriched 100-300 fold (p<0.0001), as depicted in FIG. 2A. The latter pattern of enrichment was likely driven by the BK channel's negatively charged outer pore residues. A selection of representative sequences was chosen for initial testing. These peptides included both moderately and highly enriched motifs.
Figure 2A:
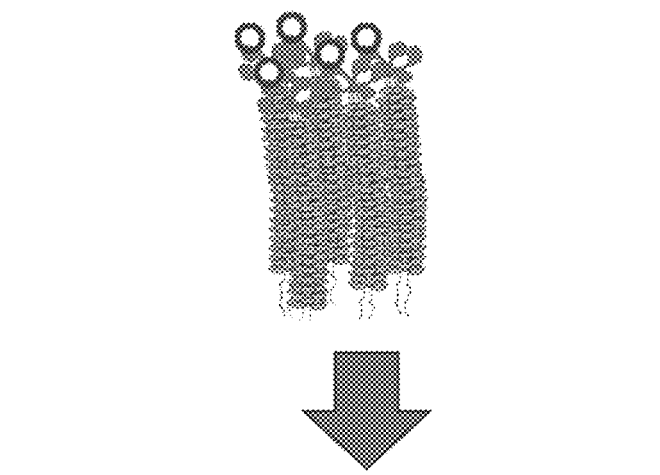
Figure 2A:
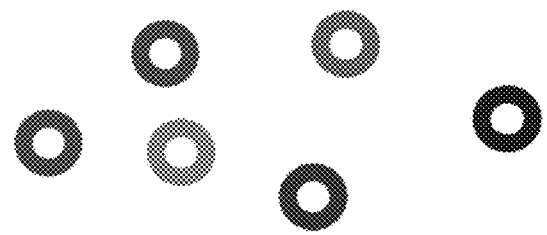
Figure 2B:
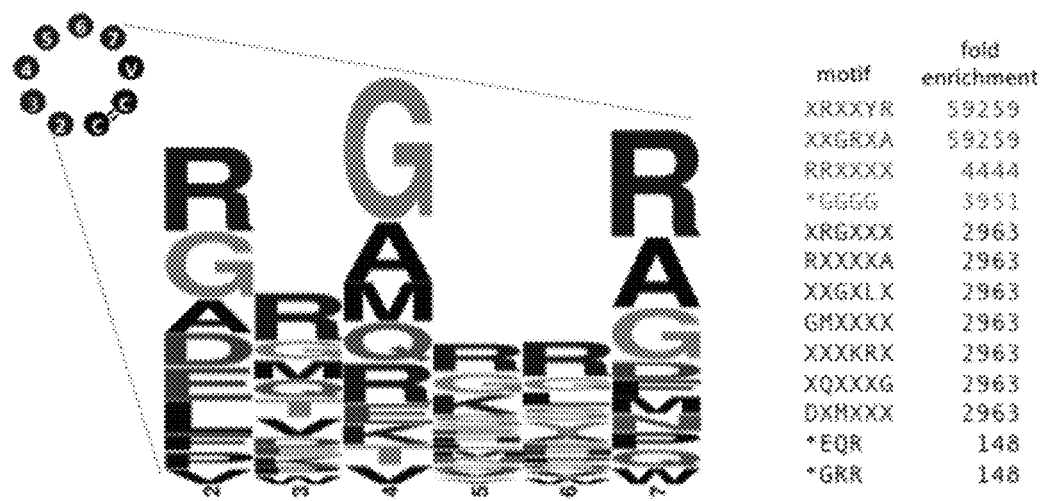
Figure 3A:
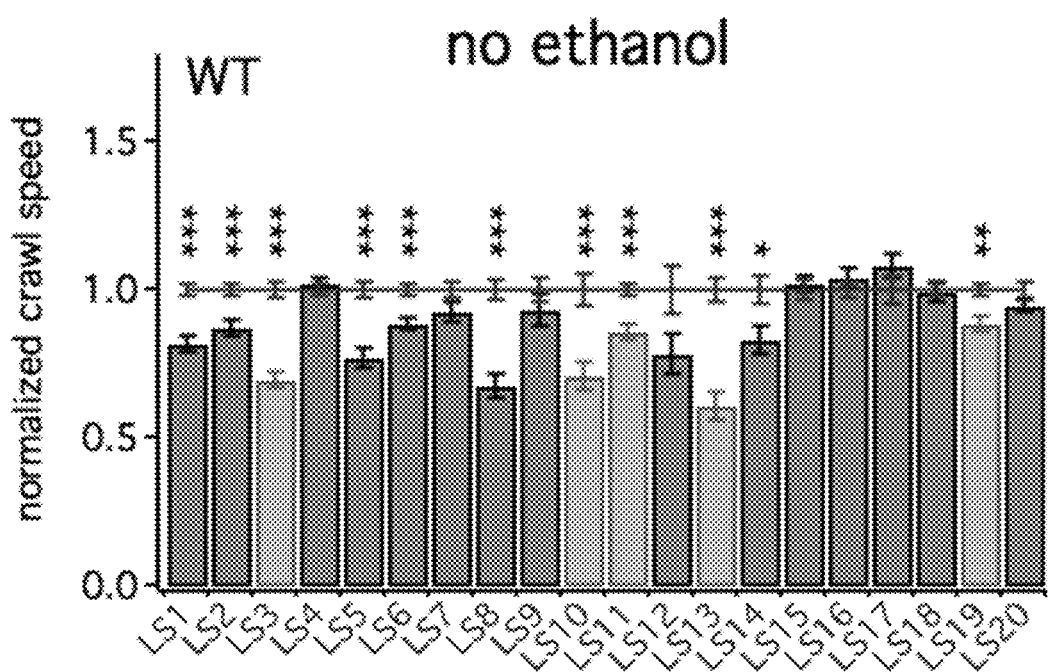
Figure 3B:
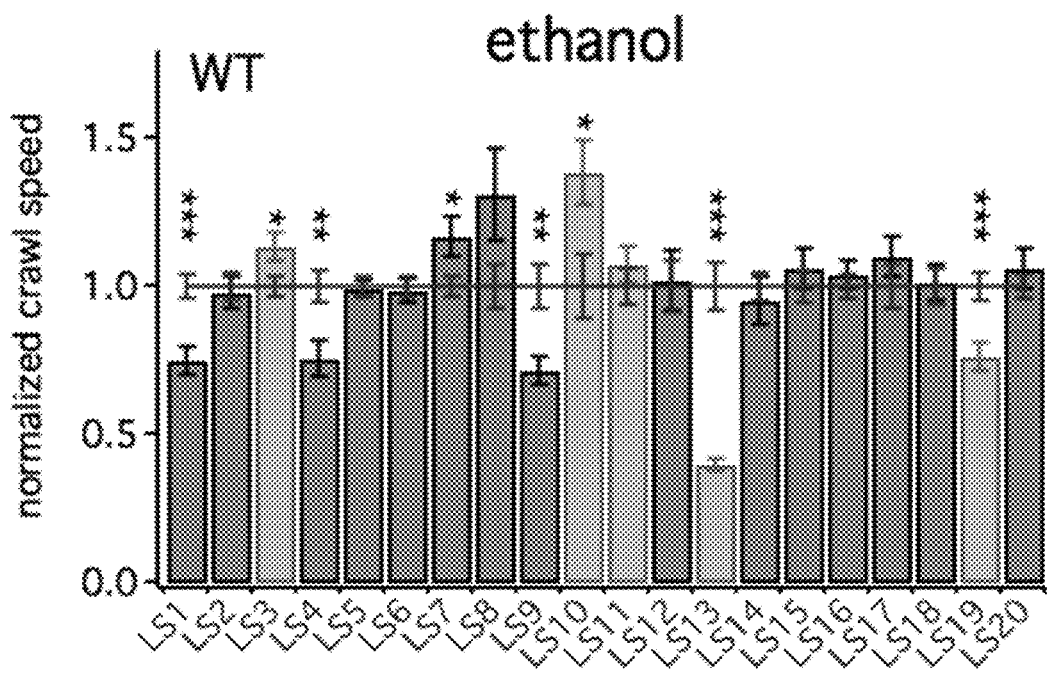
Figure 3C:
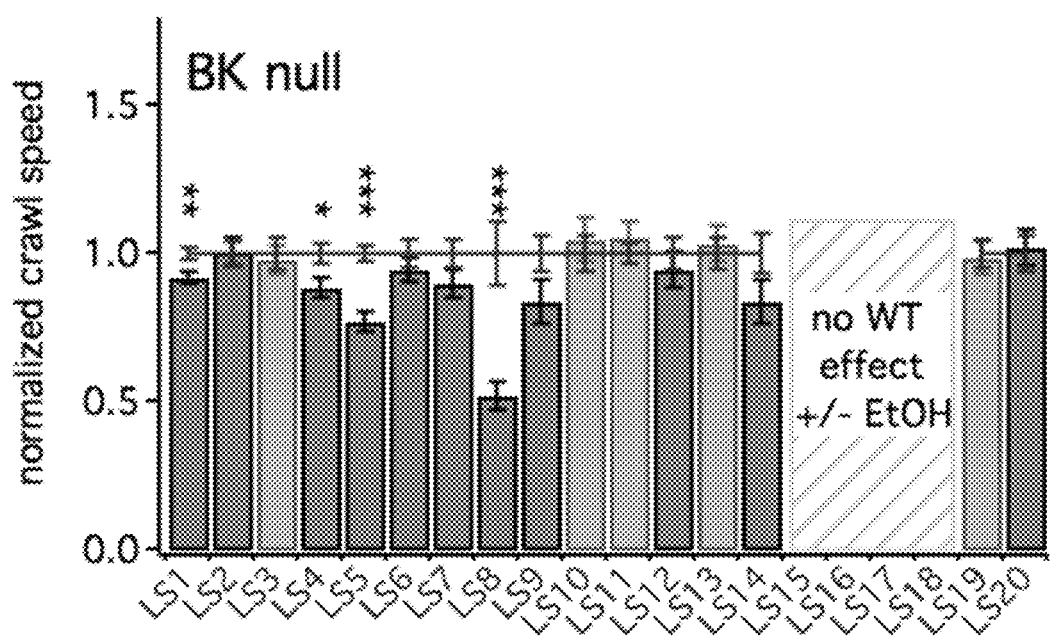
Figure 5A:
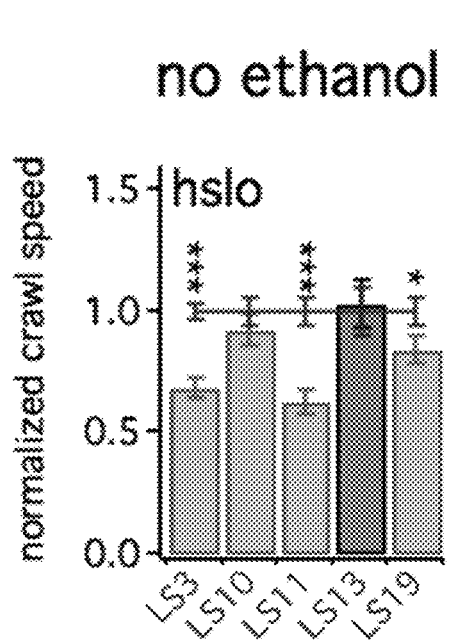
FIGS. 5A-5C. Selected peptides showed functional activity in BK channel-humanized worms. Worms expressing the ZERO isoform of the human BKα channel on a slo-1 null background were incubated with 750 µM peptide or vehicle (NGM) for 30 minutes. Post-incubation crawl speed was assessed before (FIG. 5A) and after a 20-minute exposure to ethanol (FIG. 5B). For all trials, peptide- and vehicle-treated worms were run in tandem. Crawl speeds were normalized to the vehicle-treated controls in each trial. Means±SEM are shown as bars (gray or turquoise) for the peptide-treated groups and as lines for the vehicle-treated groups (maroon). Student's t-tests compared the peptide-treated vs. vehicle-treated worms run in tandem; ***p<0.001, *p<0.05, N>60. Four peptides showed significant effects (turquoise).
Figure 5B:
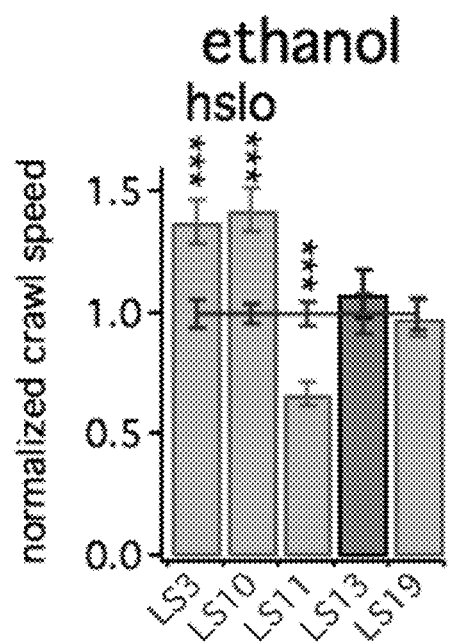
Figure 5C:
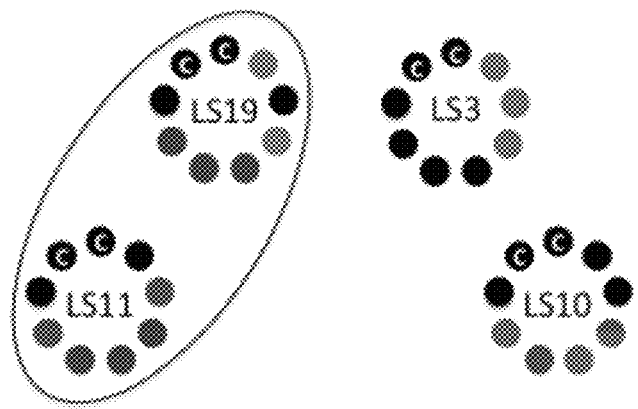
Figure 7A:
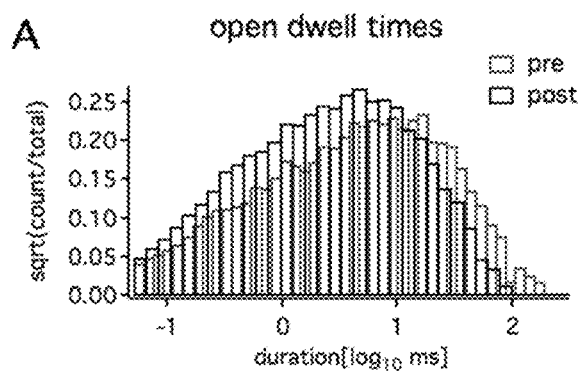
FIGS. 7A-7C. LS3 alters open and closed dwell times of the human BK channel. Single human BKα channels (ZERO isoform) expressed in HEK293 cells were recorded in inside-out patches. Intracellular calcium held at 750 nM.
Figure 7B:
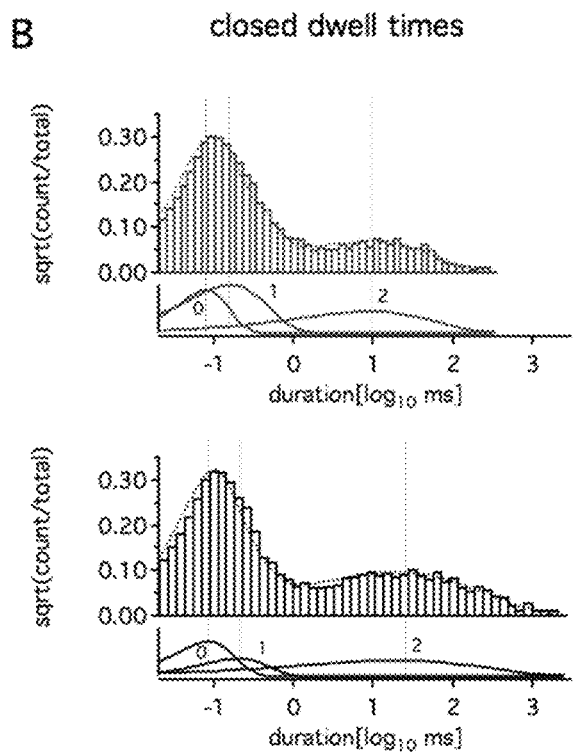
Figure 7C:
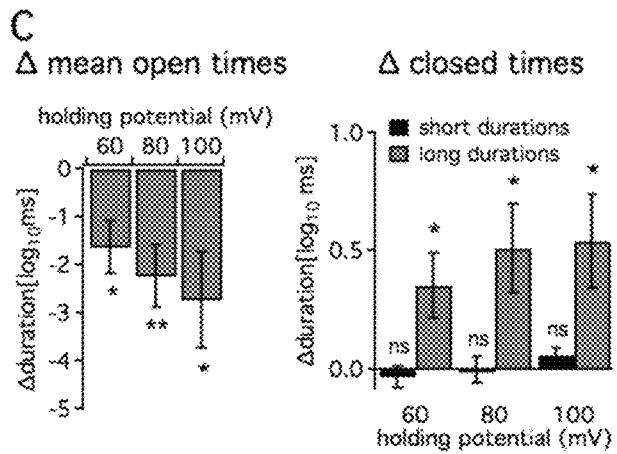
Figure 8A:
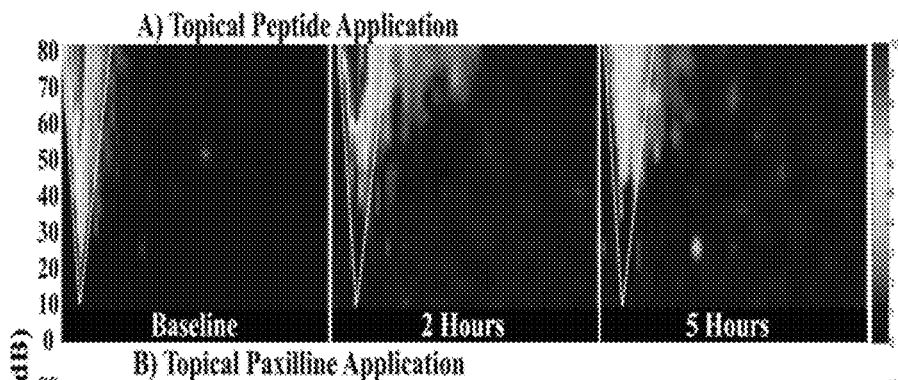
FIGS. 8A-8F. Topical and systemic application of LS3 suppresses sound evoked activity from the mouse auditory midbrain. Baseline eRFs, from between 41-47 electrode sites, were typically V-shaped with varying amounts of spontaneous activity as shown in FIGS. 8A-8C. Total spike counts within the eRF, as denoted by the white lines, were measured before and after topical application of 1 µL of a 10 µM stock of LS3 to the surface of the IC (FIG. 8A).
Figure 8B:
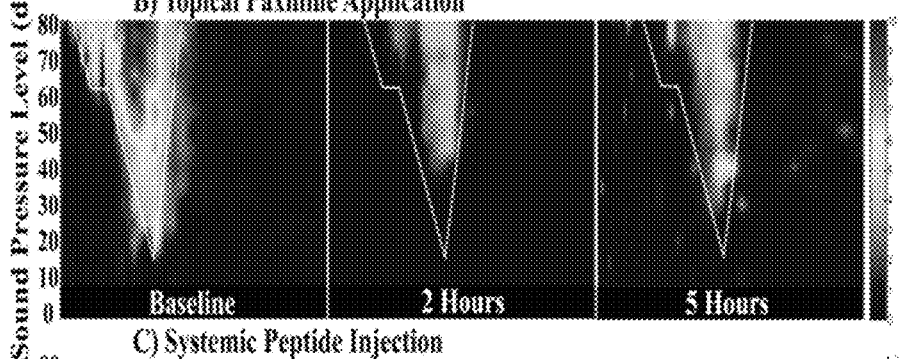
Figure 8C:
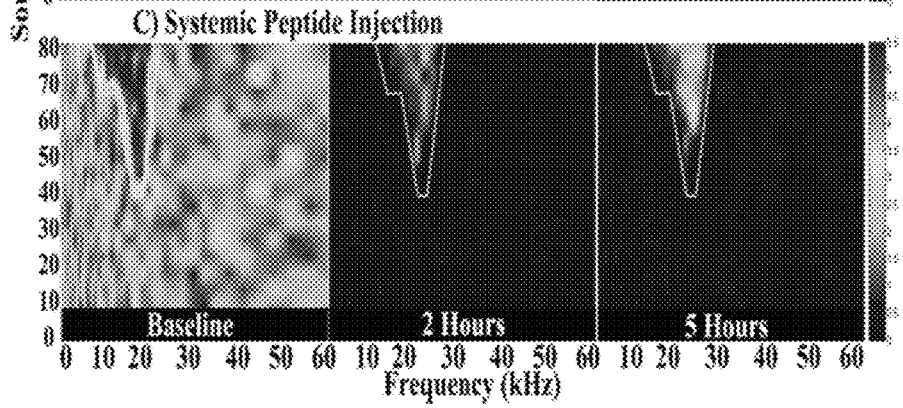
Figure 8D:
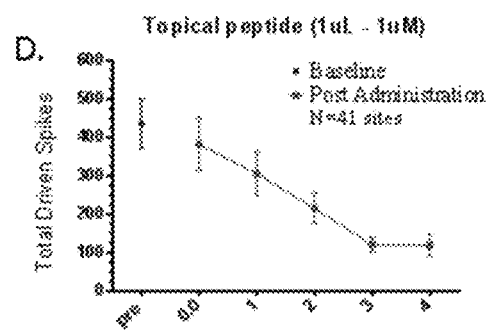
Figure 8E:
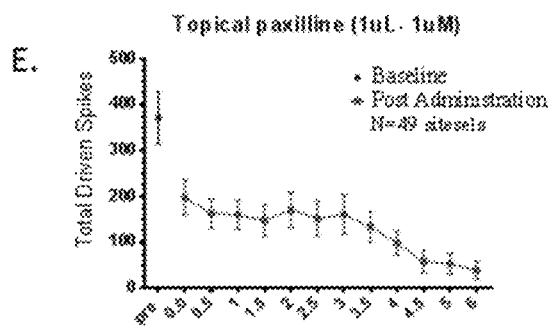
Figure 8F:
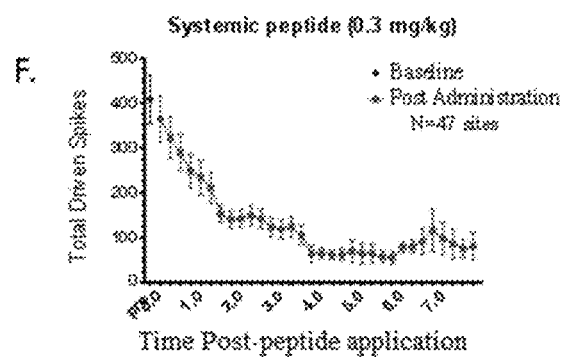
Figure 9D:
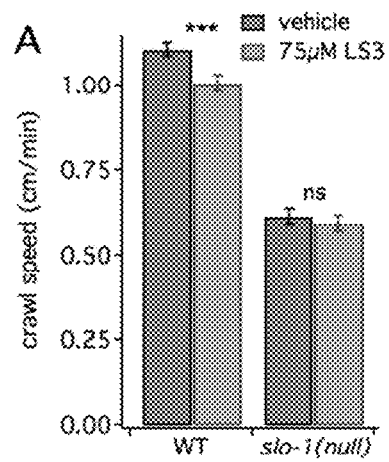
Figure 9D:
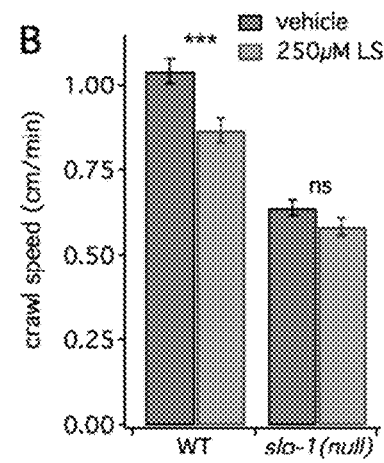
Figure 9D:
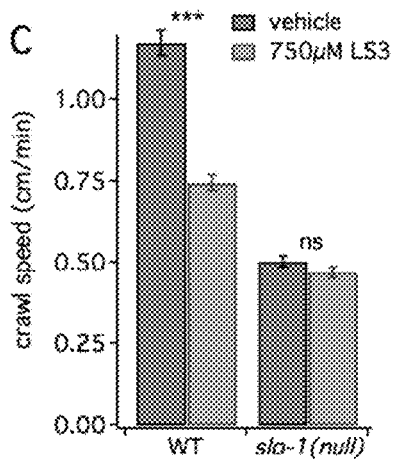
Figure 9D:
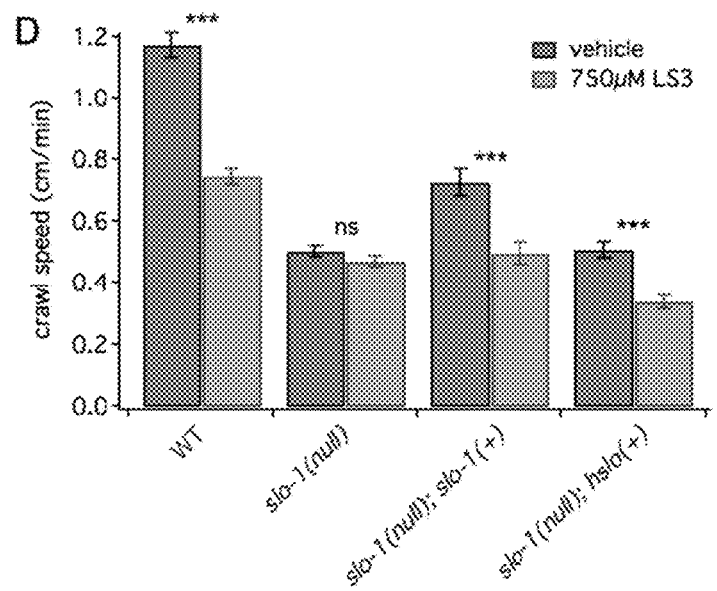
Figure 10:
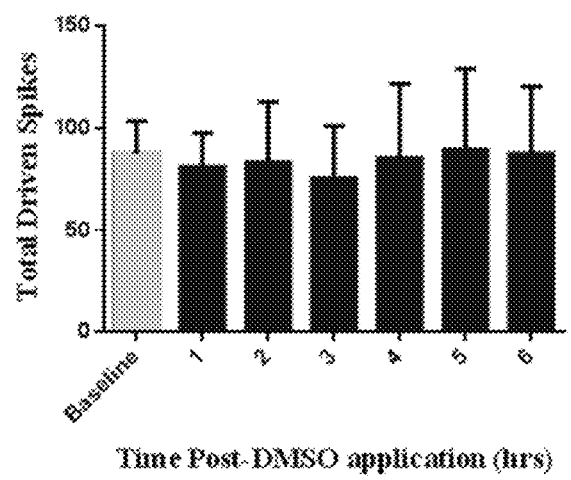
FIG. 10. Topical 1% DMSO driven spike counts taken from receptive field area defined during baseline block. Topical application of 1 uL of 1% DMSO does not alter sound evoked activity from the mouse auditory midbrain. Total spike counts (for 9 units) within the eRF were measured before and up to 6 hours after topical application of DMSO. eFRAs were measured at 1 hour intervals and even after 6 hours, driven activity remained stable (N=1).
Figure 11A:
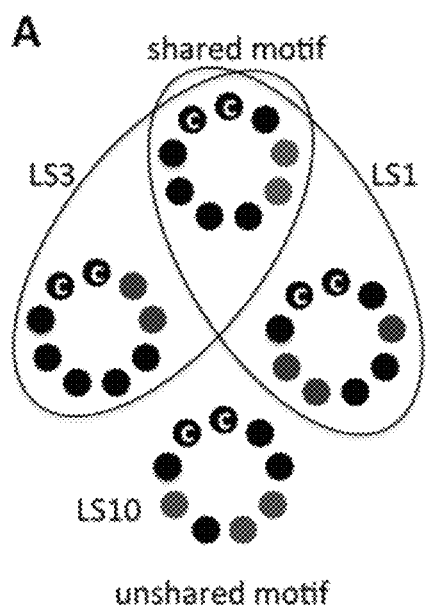
FIGS. 11A-11C. The 9-amino acid peptides with an N- and C-terminal disulfide bond express motifs that were highly enriched in a screen for BK channel targeted peptides (FIG. 11A). 500 nM LS1 (SEQ ID NO:1) and LS3 (SEQ ID NO:3) suppress opening of human BKα (ZERO) expressed in HEK293 cells (FIG. 11B); all 3 peptides (LS1, LS3, and LS10) reduce mean open times (FIG. 11C). 60 mV shown. N=6-12. Dotted line indicates baseline (FIGS. 11B and 11C).
Figure 11B:
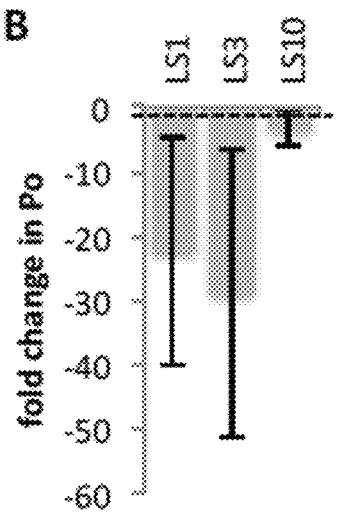
Figure 11C:
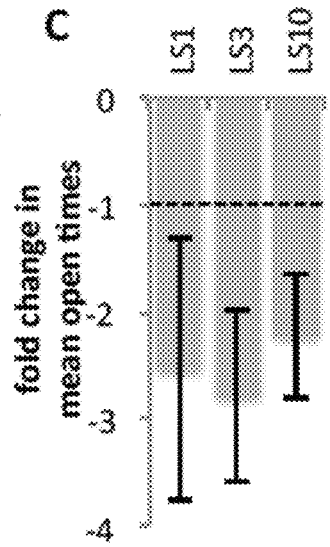
Figure 12A:
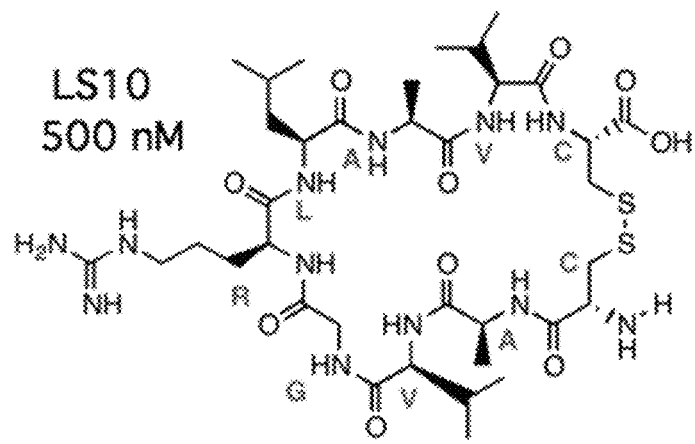
Figures 1, 12B:
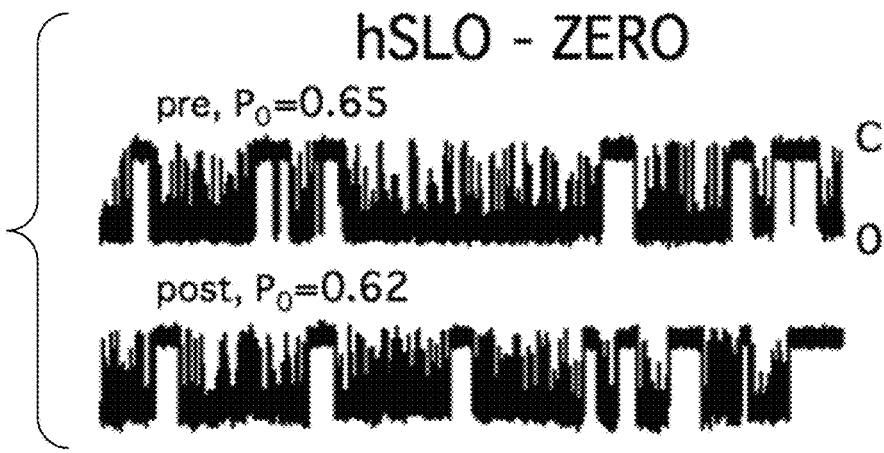
Figures 2, 12B:
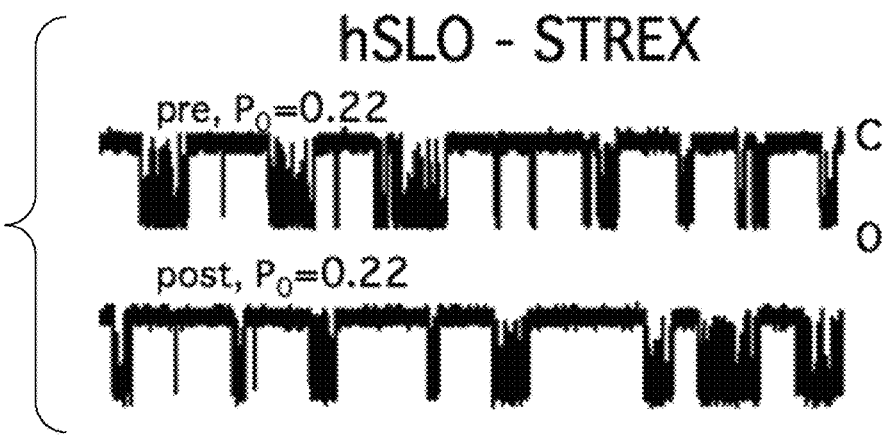
Figure 12C:
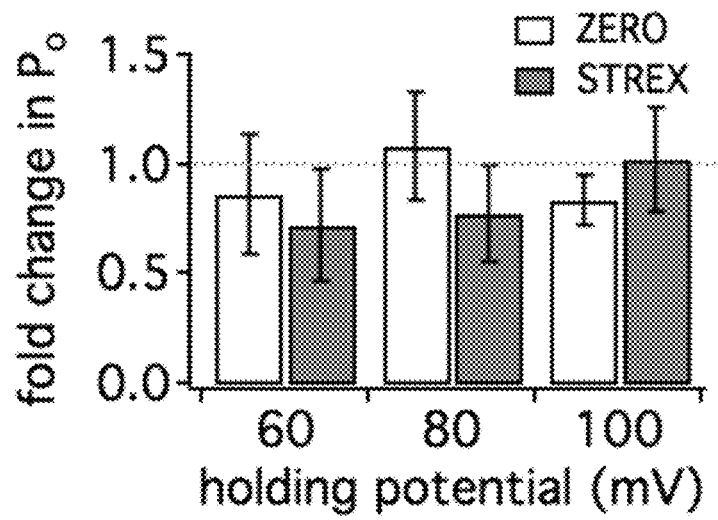
Figure 12D:
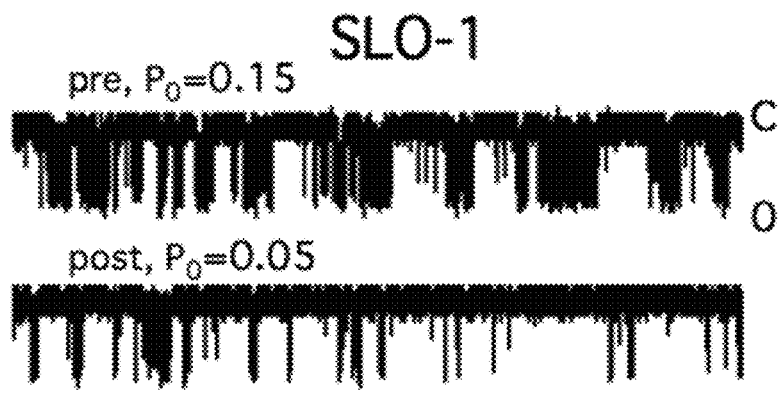
Figure 12E:
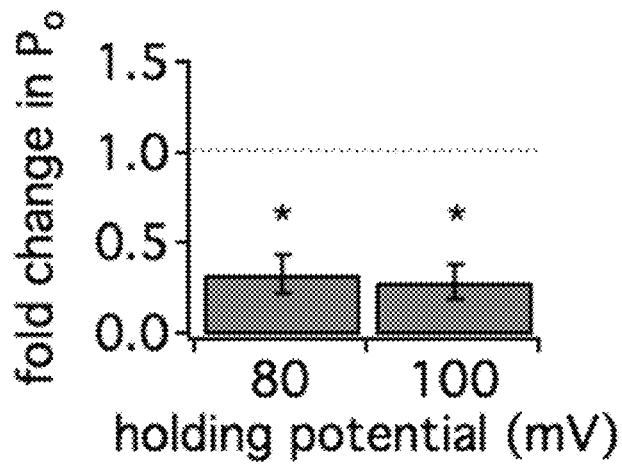
Figure 13B:
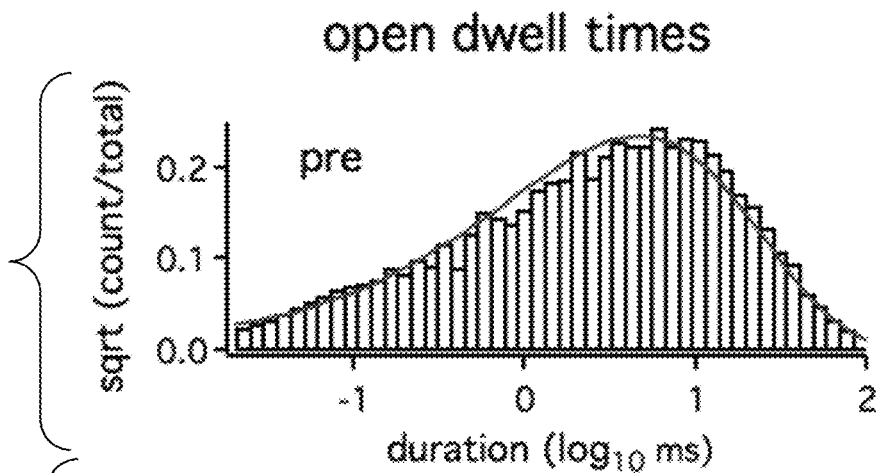
Figure 13B:
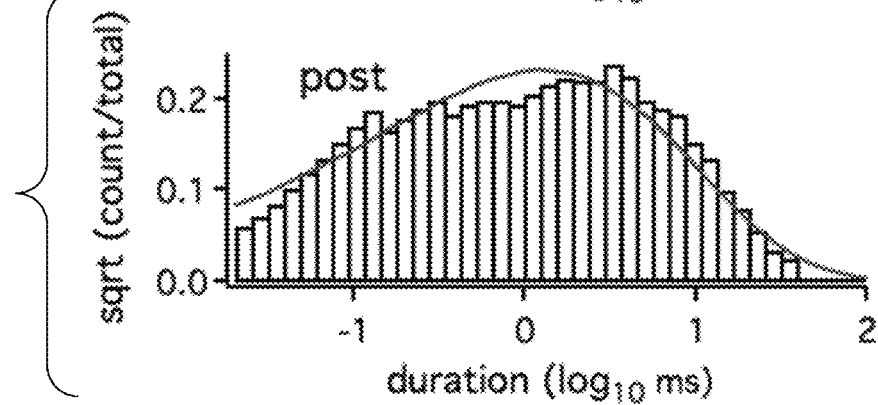
Figure 13B:
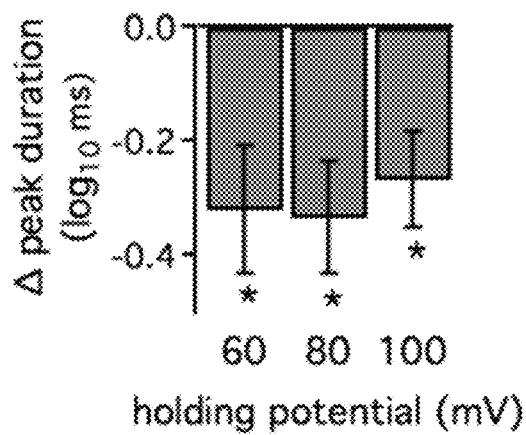
Figures 1, 13C:
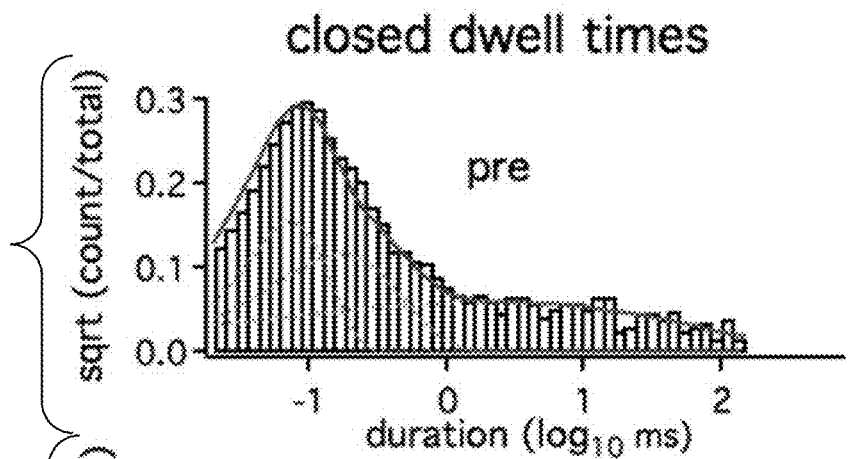
Figures 2, 13C:
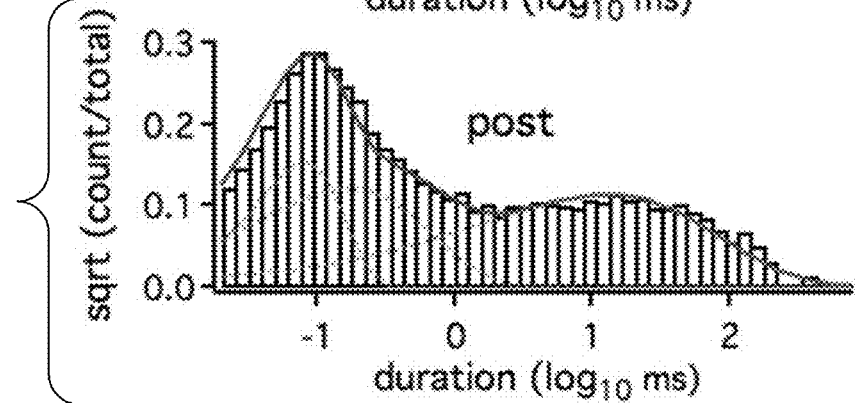
Figures 1, 13D:
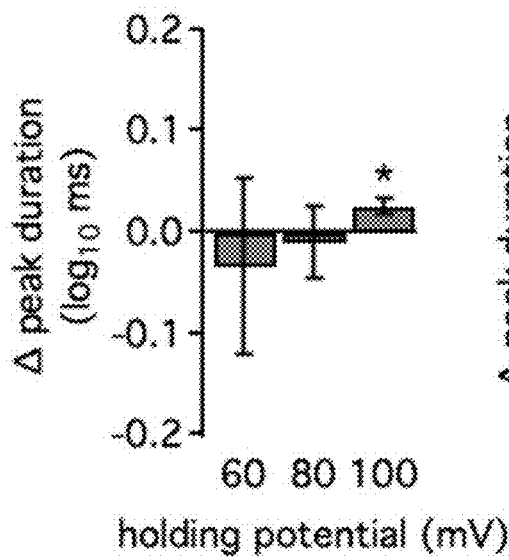
Figures 2, 13D:
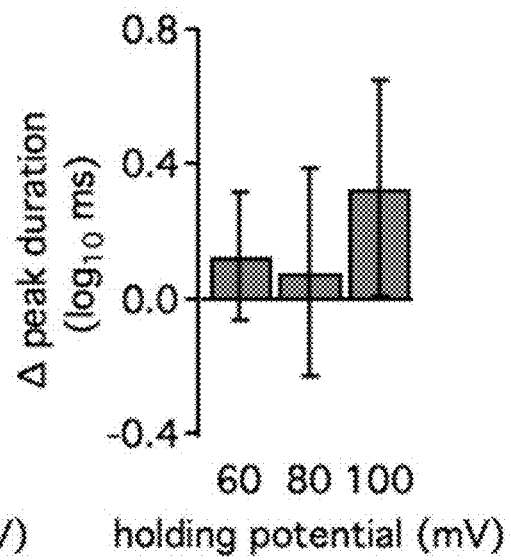
Figure 14B:
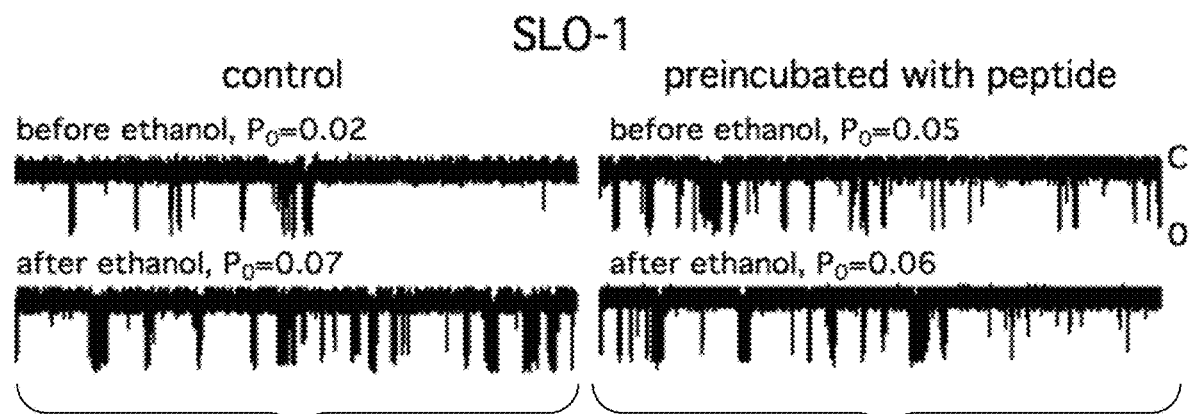
Figure 14B:
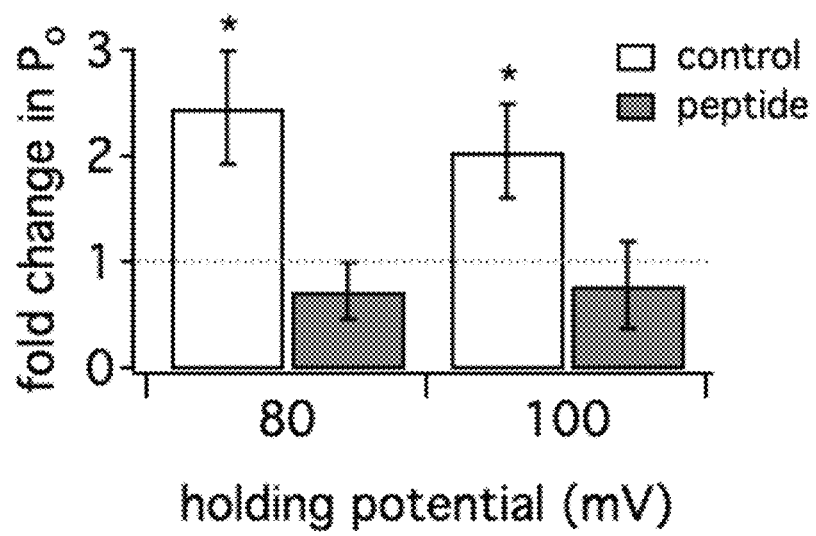

SEQ ID NO:1 is CARGVYRVC (lab designation: pskan1; also referred to as LS1), which is one embodiment of the peptide of the invention.
SEQ ID NO:2 is CRVAHRAVC (pskan2; also referred to as LS2), which is one embodiment of the peptide of the invention.
SEQ ID NO:3 is CRRGLVQVC (pskan3; also referred to as LS3), which is one embodiment of the peptide of the invention.
SEQ ID NO:4 is CPPGRGAVC (pskan4; also referred to as LS4), which is one embodiment of the peptide of the invention.
SEQ ID NO:5 is CGMTKRPVC (pskan5; also referred to as LS5), which is one embodiment of the peptide of the invention.
SEQ ID NO:6 is CDEMNWWVC (pskan21; also referred to as LS6), which is one embodiment of the peptide of the invention.
SEQ IDNO:7 is CERRMYRVC (pskan7; also referred to as LS7), which is one embodiment of the peptide of the invention.
SEQ ID NO:8 is CRRAYEMVC (pskan8; also referred to as LS8), which is one embodiment of the peptide of the invention.
SEQ ID NO:9 is CRRKRHAVC (pskan9; also referred to as LS9), which is one embodiment of the peptide of the invention.
SEQ ID NO:10 is CAVGRLAVC (pskan10; also referred to as LS10), which is one embodiment of the peptide of the invention.
SEQ ID NO:11 is CLQEQRGVC (pskan11; also referred to as LS11), which is one embodiment of the peptide of the invention.
SEQ ID NO:12 is CRKQGRRVC (pskan12; also referred to LS12), which is one embodiment of the peptide of the invention.
SEQ ID NO:13 is CEGRRARVC (pskan13; also referred to LS13), which is one embodiment of the peptide of the invention.
SEQ ID NO:14 is CLDGKLDVC (pskan14; also referred to as LS14), which is one embodiment of the peptide of the invention.
SEQ ID NO:15 is CGGGGSRVC (pskan15; also referred to as LS15), which is one embodiment of the peptide of the invention.
SEQ ID NO:16 is CFTGGGGVC (pskan16; also referred to LS16), which is one embodiment of the peptide of the invention.
SEQ ID NO:17 is CVWVKRNVC (pskan17; also referred to as LS17), which is one embodiment of the peptide of the invention.
SEQ ID NO:18 is CGMASSFVC (pskan18; also referred to as LS18), which is one embodiment of the peptide of the invention.
SEQ ID NO:19 is CDTMEQRVC (pskan19; also referred to as LS19), which is one embodiment of the peptide of the invention.
SEQ ID NO:20 is CGQQSPGVC (pskan20; also referred to s LS20), which is one embodiment of the peptide of the invention.
SEQ ID NO:21 is CWKSRWYVC (pskan6), which is one embodiment of the peptide of the invention.
SEQ ID NO:22 is CTQAETRVC (pskan22), which is one embodiment of the peptide of the invention.
SEQ ID NO:23 is CPKPNNTVC (pskan23), which is one embodiment of the peptide of the invention.
SEQ ID NO:24 is CVRAPPSVC (pskan24), which is one embodiment of the peptide of the invention.
SEQ ID NO:25 is CQAREVLVC (pskan25), which is one embodiment of the peptide of the invention.
SEQ ID NO:26 is CSEWPQNVC (pskan26), which is one embodiment of the peptide of the invention.
SEQ ID NO:27 is the formula CXXXXXXVC (SEQ ID NO:27), which is one embodiment of the peptide of the invention, wherein X is any natural or non-natural amino acid.
SEQ ID NO:28 is the enriched motif XRXXYR, which is one embodiment of the peptide of the invention, wherein X is any natural or non-natural amino acid.

SEQ ID NO:29 is the enriched motif XRGXXX, which is one embodiment of the peptide of the invention, wherein X is any natural or non-natural amino acid.

SEQ ID NO:30 is the enriched motif RRXXXX, which is one embodiment of the peptide of the invention, wherein X is any natural or non-natural amino acid.

SEQ ID NO:31 is the enriched motif RXXXXA, which is one embodiment of the peptide of the invention, wherein X is any natural or non-natural amino acid.

SEQ ID NO:32 is the enriched motif XXGRXA, which is one embodiment of the peptide of the invention, wherein X is any natural or non-natural amino acid.

SEQ ID NO:33 is the enriched motif XXGXLX, which is one embodiment of the peptide of the invention, wherein X is any natural or non-natural amino acid.

SEQ ID NO:34 is the enriched motif GMXXXX, which is one embodiment of the peptide of the invention, wherein X is any natural or non-natural amino acid.

SEQ ID NO:35 is the enriched motif XXXKRX, which is one embodiment of the peptide of the invention, wherein X is any natural or non-natural amino acid.

SEQ ID NO:36 is the enriched motif XQXXXG, which is one embodiment of the peptide of the invention, wherein X is any natural or non-natural amino acid.

SEQ ID NO:37 is the enriched motif DXMXXX, which is one embodiment of the peptide of the invention, wherein X is any natural or non-natural amino acid.

SEQ ID NO:38 is the enriched motif EQR, which is one embodiment of the peptide of the invention, wherein X is any natural or non-natural amino acid.

SEQ ID NO:39 is the enriched motif GRR, which is one embodiment of the peptide of the invention, wherein X is any natural or non-natural amino acid.

SEQ ID NO:40 is the enriched motif GGGG, which is one embodiment of the peptide of the invention, wherein X is any natural or non-natural amino acid.

SEQ ID NO:41 is the formula CXRXXYRVC, which is one embodiment of the peptide of the invention, wherein X is any natural or non-natural amino acid.

SEQ ID NO:42 is the formula CXRGXXXVC, which is one embodiment of the peptide of the invention, wherein X is any natural or non-natural amino acid.

SEQ ID NO:43 is the formula CRRXXXXVC, which is one embodiment of the peptide of the invention, wherein X is any natural or non-natural amino acid.

SEQ ID NO:44 is the formula CRXXXXAVC, which is one embodiment of the peptide of the invention, wherein X is any natural or non-natural amino acid.

SEQ ID NO:45 is the formula CXXGRXAVC, which is one embodiment of the peptide of the invention, wherein X is any natural or non-natural amino acid.

SEQ ID NO:46 is the formula CXXGXLXVC, which is one embodiment of the peptide of the invention, wherein X is any natural or non-natural amino acid.

SEQ ID NO:47 is the formula CGMXXXXVC, which is one embodiment of the peptide of the invention, wherein X is any natural or non-natural amino acid.

SEQ ID NO:48 is the formula CXXXKRXVC, which is one embodiment of the peptide of the invention, wherein X is any natural or non-natural amino acid.

SEQ ID NO:49 is the formula CXQXXXGVC, which is one embodiment of the peptide of the invention, wherein X is any natural or non-natural amino acid.

SEQ ID NO:50 is the formula CDXMXXXVC, which is one embodiment of the peptide of the invention, wherein X is any natural or non-natural amino acid.

SEQ ID NO:51 is the formula CEQRXXXVC, which is one embodiment of the peptide of the invention, wherein X is any natural or non-natural amino acid.

SEQ ID NO:52 is the formula CXEQRXXVC, which is one embodiment of the peptide of the invention, wherein X is any natural or non-natural amino acid.

SEQ ID NO:53 is the formula CXXEQRXVC, which is one embodiment of the peptide of the invention, wherein X is any natural or non-natural amino acid.

SEQ ID NO:54 is the formula CXXXEQRVC, which is one embodiment of the peptide of the invention, wherein X is any natural or non-natural amino acid.

SEQ ID NO:55 is the formula CGRRXXXVC, which is one embodiment of the peptide of the invention, wherein X is any natural or non-natural amino acid.

SEQ ID NO:56 is the formula CXGRRXXVC, which is one embodiment of the peptide of the invention, wherein X is any natural or non-natural amino acid.

SEQ ID NO:57 is the formula CXXGRRXVC, which is one embodiment of the peptide of the invention, wherein X is any natural or non-natural amino acid.

SEQ ID NO:58 is the formula CXXXGRRVC, which is one embodiment of the peptide of the invention, wherein X is any natural or non-natural amino acid.

SEQ ID NO:59 is the formula CGGGGXXVC, which is one embodiment of the peptide of the invention, wherein X is any natural or non-natural amino acid.

SEQ ID NO:60 is the formula CXGGGGXVC, which is one embodiment of the peptide of the invention, wherein X is any natural or non-natural amino acid.

SEQ ID NO:61 is the formula CXXGGGGVC, which is one embodiment of the peptide of the invention, wherein X is any natural or non-natural amino acid.

DETAILED DESCRIPTION OF THE INVENTION

The present convention concerns peptides that modulate large conductance $Ca^{2+}$ activated $K^+$ (BK) channel activity, compositions containing the peptides, and methods of using the peptides and compositions for the treatment and prevention of diseases and disorders. In some embodiments, the peptide comprises, or consists of, an amino acid sequence listed in Table 1, or a functional fragment or variant thereof.

TABLE 1

Peptide sequences

| Name | Peptide amino acid sequence | Sequence ID | Enriched motifs |
|---|---|---|---|
| LS1 (a.k.a. pskan1) | CARGVYRVC | SEQ ID NO: 1 | XRXXYR (SEQ ID NO: 28), XRGXXX (SEQ ID NO: 29) |
| LS2 (a.k.a. pskan2) | CRVAHRAVC | SEQ ID NO: 2 | RXXXXA (SEQ ID NO: 31) |

TABLE 1-continued

Peptide sequences

| Name | Peptide amino acid sequence | Sequence ID | Enriched motifs |
|---|---|---|---|
| LS3 (a.k.a pskan3) | CRRGLVQVC | SEQ ID NO: 3 | XRGXXX (SEQ ID NO: 29), RRXXXX (SEQ ID NO: 30) |
| LS4 (a.k.a. pskan4) | CPPGRGAVC | SEQ ID NO: 4 | XXGRXA (SEQ ID NO: 32) |
| LS5 (a.k.a. pskan5) | CGMTKRPVC | SEQ ID NO: 5 | GMXXXX (SEQ ID NO: 34), XXXKRX (SEQ ID NO: 35) |
| LS6 (a.k.a. pskan21) | CDEMNWWVC | SEQ ID NO: 6 | DXMXXX (SEQ ID NO: 37) |
| LS7 (a.k.a. pskan7) | CERRMYRVC | SEQ ID NO: 7 | XRXXYR (SEQ ID NO: 28) |
| LS8 (a.k.a. pskan8) | CRRAYEMVC | SEQ ID NO: 8 | RRXXXX (SEQ ID NO: 30) |
| LS9 (a.k.a. pskan9) | CRRKRHAVC | SEQ ID NO: 9 | RRXXXX (SEQ ID NO: 30), RXXXXA (SEQ ID NO: 31) |
| LS10 (a.k.a. pskan10) | CAVGRLAVC | SEQ ID NO: 10 | XXGRXA (SEQ ID NO: 32), XXGXLX (SEQ ID NO: 33) |
| LS11 (a.k.a. pskan11) | CLQEQRGVC | SEQ ID NO: 11 | EQR (SEQ ID NO: 38), XQXXXG (SEQ ID NO: 36) |
| LS12 (a.k.a. pskan12) | CRKQGRRVC | SEQ ID NO: 12 | GRR (SEQ ID NO: 39) |
| LS13 (a.k.a. pskan13) | CEGRRARVC | SEQ ID NO: 13 | GRR (SEQ ID NO: 39) |
| LS14 (a.k.a. pskan14) | CLDGKLDVC | SEQ ID NO: 14 | XXGXLX (SEQ ID NO: 33) |
| LS15 (a.k.a. pskan15) | CGGGGSRVC | SEQ ID NO: 15 | GGGG (SEQ ID NO: 40) |
| LS16 (a.k.a. pskan16) | CFTGGGVC | SEQ ID NO: 16 | GGGG (SEQ ID NO: 40) |
| LS17 (a.k.a. pskan17) | CVWVKRNVC | SEQ ID NO: 17 | XXXKRX (SEQ ID NO: 35) |
| LS18 (a.k.a. pskan18) | CGMASSFVC | SEQ ID NO: 18 | GMXXXX (SEQ ID NO: 34) |
| LS19 (a.k.a. pskan19) | CDTMEQRVC | SEQ ID NO: 19 | EQR (SEQ ID NO: 38), DXMXXX (SEQ ID NO: 37) |
| LS20 (a.k.a. pskan20) | CGQQSPGVC | SEQ ID NO: 20 | XQXXXG (SEQ ID NO: 36) |
| Pskan6 | CWKSRWYVC | SEQ ID NO: 21 | |
| Pskan22 | CTQAETRVC | SEQ ID NO: 22 | |
| Pskan23 | CPKPNNTVC | SEQ ID NO: 23 | |

TABLE 1-continued

Peptide sequences

| Name | Peptide amino acid sequence | Sequence ID | Enriched motifs |
|---|---|---|---|
| Pskan24 | CVRAPPSVC | SEQ ID NO: 24 | |
| Pskan25 | CQAREVLVC | SEQ ID NO: 25 | |
| Pskan26 | CSEWPQNVC | SEQ ID NO: 26 | |

In Table 1, X is any natural or non-natural amino acid.

One aspect of the invention concerns a peptide comprising an amino acid sequence of Table 1, i.e., selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CDEMNWWVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CWKSRWYVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26), or a functional fragment or variant of any one of the foregoing amino acid sequences.

The peptides of the invention may be a linear peptide, or a cyclic (non-linear) peptide. Cyclic peptides are polypeptide chains in which the amino termini and carboxyl termini; amino termini and side chain; carboxyl termini and side chain; or side chain and side chain are linked (e.g., with a covalent bond) that generates the ring (see Joo S, "Cyclic Peptides as Therapeutic Agents and Biochemical Tools," *Biomol Ther* (*Seoul*), 2012 January; 20(1): 19-26, which is incorporated herein by reference). Cyclic peptides can generally be classified according to the types of bonds that comprise the ring: homodetic cyclic peptides, cyclic isopeptides, cyclic depsipeptides, and bicyclic peptides. Homodetic cyclic peptides, such as cyclosporine A, are those in which the ring is composed exclusively of normal peptide bonds (i.e., between the alpha carboxyl of one residue to the alpha amine of another). Cyclic isopeptides contain at least one non-alpha amide linkage, such as a linkage between the side chain of one residue to the alpha carboxyl group of another residue, as in microcystin and bacitracin. Cyclic depsipeptides, such as aureobasidin A and HUN-7293, have at least one lactone (ester) linkage in place of one of the amides. Some cyclic depsipeptides are cyclized between the C-terminal carboxyl and the side chain of a Thr or Ser residue in the chain, such as kahalalide F, theonellapeptolide, and didemnin B. Bicyclic peptides such as the amatoxin amanitin and the phallotoxin phalloidin contain a bridging group, generally between two of the side chains. In the amatoxins, this bridge is formed as a thioether between the Trp and Cys residues. Other bicyclic peptides include echinomycin, triostin A, and Celogentin C. There are a number of cyclic peptide hormones which are cyclized through a disulfide bond between two cysteines, as in somatostatin and oxytocin.

Depending on the cyclization position, there are several methods to synthesize cyclic peptides: head-to-tail, side-chain-to-side-chain, head-to-side-chain, and side-chain-to-tail (see figure below). While head-to-tail cycles are usually formed by amide bond formation, side-chain-to-side-chain cycles are most often synthesized via Cys-Cys or amide bond formation.

The peptide disulfide bridge strategy readily synthesizes two thiol (SH) groups from the side chain of cysteine or cysteine analogues. This strategy enables either specific intra- or intermolecular oxidation using appropriate protecting group chemistry to avoid undesired linkage. The reaction can be followed by HPLC and MALDI TOF mass spectrometry with the linear peptide losing two mass units (2H) on cyclization.

In general, a disulfide bridge can be formed intermolecularly (two peptide molecules are linked via the disulfide bridge), resulting in either: homodimers (two identical peptides) or heterodimers (two different peptides); or intramolecularly (cyclization within one peptide molecule). While head-to-tail cyclization is usually formed by using an amide bond formation, side-chain-to-side-chain peptide cyclization is most often synthesized via Cys-Cys or amide bond formation. Peptides with two or more disulfide bridges require selective protection of the cysteine side chains to ensure that the correct disulfide bridges are formed. Peptides with up to 4 disulfide bonds in one peptide can be produced using site-specific orthogonal chemistry or thermodynamic stability methods. Contact us to discuss your project details.

Cyclic peptides can also be synthesized by linking the N-terminus of the peptide to the C-terminus via an amide bond. The amino side chains of Lys and Orn and the carboxyl side chains of Asp and Glu can also be used to construct cyclic peptides via an amide bond. Amide bond is more chemically stable than disulfide bridge. Depending on functional groups of a peptide, cyclic peptide synthesis can be formed in four different ways: head-to-tail between N-terminus and C-terminus; head-to-side chain between N-terminus and an internal COOH (e.g., the β-COOH-group of Asp or γ-COOH-group of Glu); side chain-to-tail between internal NH2s and C-terminus (e.g., the ε-NH2-group of Lys); and side-chain-to-side-chain between an internal NH2 and an internal COOH (e.g., the ε-NH2-group of Lys with either the β-COOH-group of Asp or γ-COOH-group of Glu). Stapled peptide synthesis and click chemistry may also be used for cyclic peptide production.

In some embodiments, the peptide has an N-terminal and C-terminal disulfide bridge (i.e., a disulfide bridge between the cysteines).

In some embodiments, the peptide comprises an amino acid sequence selected from among: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26). In some embodiments, the peptide has an N-terminal and C-terminal disulfide bridge (i.e., a disulfide bridge between the cysteines).

In some embodiments, the peptide consists of an amino acid sequence selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26). In some embodiments, the peptide has an N-terminal and C-terminal disulfide bridge (i.e., a disulfide bridge between the cysteines).

Several motifs have been identified among the peptides. In some embodiments, the peptide comprises an amino acid sequence comprising the formula CXXXXXXVC (SEQ ID NO:27), wherein X is any natural or non-natural amino acid, and having an N-terminal and C-terminal disulfide bridge (i.e., a disulfide bridge between the cysteines). In some embodiments, the peptide comprises an amino acid sequence consisting of the formula CXXXXXXVC (SEQ ID NO:27), wherein X is any natural or non-natural amino acid. In some embodiments, the peptide has an N-terminal and C-terminal disulfide bridge (i.e., a disulfide bridge between the cysteines).

Enriched motifs are listed in Table 1. Furthermore, the following thirteen enriched motifs have been identified: XRXXYR (SEQ ID NO:28), XRGXXX (SEQ ID NO:29), RRXXXX (SEQ ID NO:30), RXXXXA (SEQ ID NO:31), XXGRXA (SEQ ID NO:32), XXGXLX (SEQ ID NO: 33), GMXXXX (SEQ ID NO:34), XXXKRX (SEQ ID NO:35), XQXXXG (SEQ ID NO:36), DXMXXX (SEQ ID NO:37), EQR (SEQ ID NO:38), GRR (SEQ ID NO:39), and GGGG (SEQ ID NO:40), wherein X is any natural or non-natural amino acid, and those motifs without an "X" can slide anywhere en bloc within the six variable amino acid positions of CXXXXXXVC (SEQ ID NO:27). Thus, in some embodiments, the peptide comprises an amino acid sequence comprising or consisting of: CXRXXYRVC (SEQ ID NO:41), CXRGXXXVC (SEQ ID NO:42), CRRXXXXVC (SEQ ID NO:43), CRXXXXAVC (SEQ ID NO:44), CXXGRXAVC (SEQ ID NO:45), CXXGXLXVC (SEQ ID NO:46), CGMXXXXVC (SEQ ID NO:47), CXXXKRXVC (SEQ ID NO:48), CXQXXXGVC (SEQ ID NO:49), CDXMXXXVC (SEQ ID NO:50), CEQRXXXVC (SEQ ID NO:51), CXEQRXXVC (SEQ ID NO:52), CXXEQRXVC (SEQ ID NO:53), CXXXEQRVC (SEQ ID NO:54), CGRRXXXVC (SEQ ID NO:55), CXGRRXXVC (SEQ ID NO:56), CXXGRRXVC (SEQ ID NO:57), CXXXGRRVC (SEQ ID NO:58), CGGGGXXVC (SEQ ID NO:59), CXGGGGXVC (SEQ ID NO:60), or CXXGGGGVC (SEQ ID NO:61), wherein X is any natural or non-natural amino acid. In some embodiments, the peptide has an N-terminal and C-terminal disulfide bridge (i.e., a disulfide bridge between the cysteines).

In some embodiments, the peptide comprises an amino acid sequence comprising, or consisting of, an enriched motif of Table 1, i.e., SEQ ID NO:28-40, wherein X is any natural or non-natural amino acid.

In some embodiments, the peptide comprises CRRGLVQVC (SEQ ID NO:3). In some embodiments, the peptide comprises an amino acid sequence consisting of CRRGLVQVC (SEQ ID NO:3). In some embodiments, the peptide has an N-terminal and C-terminal disulfide bridge (i.e., a disulfide bridge between the cysteines).

In some embodiments, the peptide is in isolated or purified form.

Peptides that comprise an indicated amino acid sequence (e.g., by numeric identifier) may further comprise additional moieties attached directly or indirectly to the amino acid sequence, such as additional amino acids, nucleic acids, or small molecules, for example. Peptides that comprise an amino acid sequence consisting of an indicated sequence (e.g., by numeric identifier) include no additional amino acids as part of that amino acid sequence, but may include other moieties attached directly or indirectly to the amino acid sequence, such as nucleic acids or small molecules, for example.

Optionally, the peptide of the invention may have a heterologous amino acid sequence or a moiety fused or otherwise coupled directly or indirectly to any portion of the amino acid sequence, which is then referred to as a polypeptide construct. In some embodiments, the heterologous moiety comprises a label that is detectable using an appropriate detection modality. For example, the detectable label may be a chemiluminescent structural element, a radioactive isotope, or an enzyme to generate a color reaction. The moiety fused to the amino acid sequence may be a nucleic acid such as a DNA or RNA molecule. Polypeptide constructs may be linear or cyclic.

The peptides of the invention may comprise chemical modifications in the side chain or at the N- and/or C-terminal for improving biological or chemical properties such as bioavailability, stability, effectivity. The modification may also provide for a detectable label, for example a chem-iluminescent structural element, one or more radioactive isotopes in one or more side chains of an amino acid in the peptide, an enzyme which is able to generate a color reaction and the like.

A large number of fluorescent and chemiluminescent compounds have been shown to be useful for labeling proteins and nucleic acids. Examples of compounds that may be used as the dye portion can include but are not limited to xanthene, anthracene, cyanine, porphyrin and coumarin dyes. Examples of xanthene dyes that may be coupled to the peptides can include but are not limited to fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 5-carboxy-2',4',5',7'-tetrachlorofluorescein (ZOE) rhodol, rhodamine, tetramethylrhodamine (TAMRA), 4,7-dichlorotetramethyl rhodamine (DTAMRA), rhodamine X (ROX) and Texas Red. Examples of cyanine dyes that may find use with the peptides include but are not limited to Cy 3, Cy 3.5, Cy 5, Cy 5.5, Cy 7 and Cy 7.5. Other dyes that may find use with the peptides can include but are not limited to energy transfer dyes, composite dyes and other aromatic compounds that give fluorescent signals. Chemiluminescent compounds that may be used with the peptides include but are not limited to dioxetane and acridinium esters. It should also be understood that ligands and dyes are not mutually exclusive groups. For instance, fluorescein is a well known example of a moiety that has been used as a fluorescent label and also as an antigen for labeled antibodies.

The heterologous amino acid sequence or moiety may have a physiological function such as an antibody or antibody fragment, scaffolds such as lipocalin, ankyrin, fibronectin, transferrin, tetranectin, adnectin, albumin, uteroglobin, or protein A, functional peptides such as transferrin, peptides useful for diagnostic applications, fluorescent polypeptide such as green fluorescent protein (GFP), or peptide tags enabling immobilization on technical surfaces, such as hexahistidine, or glutathione-S-transferase (GST).

In some embodiments, the polypeptide construct is a fusion polypeptide comprising a first amino acid sequence of the invention and a second amino acid sequence fused directly or indirectly to the first amino acid sequence. Thus, in some embodiments, the fusion polypeptide comprises a first amino acid sequence of the invention, e.g., an amino acid sequence selected from the group consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26), or an amino acid sequence having one or more conservative substitutions or deletions of any one of the foregoing, and a second amino acid sequence fused directly or indirectly to the first amino acid sequence. In some embodiments, the peptide has an N-terminal and C-terminal disulfide bridge (i.e., a disulfide bridge between the cysteines). The second amino acid sequence may be fused to the amino-terminus (N-terminus) or carboxyl-terminus (C-terminus) of the first amino acid sequence. The fusion may be direct or indirect through a linker (e.g., a chemical element linker or amino acid linker). The first amino acid sequence may be identical to or different from the second amino acid sequence. The fusion polypeptide may further comprise one or more additional amino acid sequences directly or indirectly fused to the first amino acid sequence or second amino acid sequence, making a "multimer".

The peptides of the invention can shuttle themselves and cargo molecules across the blood-brain barrier of the mammalian brain. Another aspect of the invention concerns a method of delivering a cargo moiety to the brain of a subject, through the blood-brain barrier (BBB), comprising administering a polypeptide construct described above to the subject, wherein the polypeptide construct comprises a peptide of the invention conjugated to the cargo moiety. The polypeptide construct can be administered to the subject by any method outside the brain, allowing the polypeptide construct bearing one or more cargo moieties to be ported into the brain of the subject through the BBB. In some embodiments, the polypeptide construct is administered intravascularly (e.g., intravenously or intra-arterially). In the delivery method, the cargo moiety can be any moiety (inclusive of moieties) that may be coupled to the peptide and not prevent the peptide from passing through the BBB. For example, the cargo moiety to be ported across the BBB may be a small molecule(s), amino acid(s), nucleic acid(s) such as DNA or RNA, detectable label(s), etc.

Examples of detectable labels that may be coupled to the peptides of the invention include, for example, fluorescent labels, chemiluminescent labels, and bioluminescent labels. Fluorescent labeling compounds that may be used are fluorescein isothiocyanate, rhodamine, phycoerythrin, phycocyanin, allophycocyanin, o-phthaldehyde, and fluorescamine. The peptide also can be detectably labeled by coupling it to a chemiluminescent compound. The presence of the chemiluminescent-tagged peptide can then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the peptide of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Typical bioluminescent compounds useful for labeling are luciferin, luciferase and aequorin.

The peptides may be produced recombinantly or synthesized. Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the polypeptide into growth medium (see U.S. Pat. No. 6,596, 509 to Bauer et al., which is hereby incorporated by reference in its entirety), the peptides can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Peptides (at least those containing peptide linkages between amino acid residues) may be synthesized by the Fmoc-polyamide mode of solid-phase peptide synthesis as disclosed by Lu et al. (1981) *J. Org. Chem.* 46, 3433-3436, and references therein. Temporary N-amino group protection is afforded by the 9-fluorenylmethyloxycarbonyl (Fmoc) group. Repetitive cleavage of this highly base-labile protecting group is achieved by using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support can be based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethylphenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized.

A "peptide" refers to a chain of two or more amino acids of any length. In some embodiments, the peptides of the invention have an overall length of between 5 and 100 amino acids, between 5 and 30 amino acids, between 5 and 12 amino acids, between 8 and 10 amino acids, or 9 amino acids. Multimers can have lengths that are multiples of these ranges. A peptide may be linear or circular (non-linear). In some embodiments, the peptide has an N-terminal and C-terminal disulfide bridge (i.e., a disulfide bridge between the cysteines).

Another aspect of the invention concerns a nucleic acid encoding any of the aforementioned peptides of the invention. Another aspect of the invention concerns an expression construct, such as a viral or non-viral vector, comprising the nucleic acid encoding any of the aforementioned peptides of the invention.

Another aspect of the invention concerns a composition comprising a peptide of the invention, a nucleic acid encoding the peptide, or an expression construct comprising the nucleic acid or expression construct; and a pharmaceutically acceptable carrier or diluent.

Another aspect of the invention concerns a method for treating a condition in a subject in need thereof, comprising administering an agent of the invention to the subject, wherein the condition is selected from among presbycusis, audiogenic seizures, alcohol addiction, cancer, and neurodegenerative disease (e.g., Alzheimer's disease (AD), Parkinson's disease (PD), Huntington's disease). The agent may be a peptide of the invention, a nucleic acid encoding the peptide, an expression construct comprising a nucleic acid encoding the peptide. The agent may be administered to the subject in a composition comprising the agent and a pharmaceutically acceptable carrier or diluent.

The agent may be administered to the subject by any route effective in delivering the agent to the desired anatomical location or locations. In some embodiments, the agent is administered systemically. In some embodiments, the agent is administered locally. In some embodiments, the agent is administered to the subject by a route selected from the group consisting of intravascular (e.g., intravenous or intra-arterial), intramuscular, intracutaneous, oral, intranasal, intra-ocular, topical, and transdermal.

The agent may be administered to the subject as therapy or prophylaxis. Thus, in some embodiments, the subject has the condition at the time the agent is administered, and the agent is administered to the subject as therapy for the condition. In other embodiments, the subject does not have the condition at the time the agent is administered, and the agent is administered to prevent or delay the onset of the condition.

Optionally, one or more additional biologically active agents are administered to the subject before, during, or after administration of the agent. For example, the one or more additional agents may have activity that is useful in treating or delaying onset of the condition. The one or more additional biologically active agents may be administered within the same composition as the agent or in separate composition. Thus, the composition may include one or more additional biologically active agents.

In some embodiments, the agent comprises a peptide of Table 1. In some embodiments, the peptide of Table 1 has an N-terminal and C-terminal disulfide bridge (i.e., a disulfide bridge between the cysteines). In some embodiments, the agent comprises a peptide comprising CRRGLVQVC (SEQ ID NO:3). In some embodiments, the agent comprises a peptide comprising an amino acid sequence consisting of CRRGLVQVC (SEQ ID NO:3).

Another aspect of the invention concerns a method for modulating BK channel activity in a cell having a BK channel in vitro or in vivo, comprising contacting the cell in vitro or in vivo with an agent of the invention. In some embodiments, the BK channel activity is BKα channel function (see, for example, Lee U S and J Cui, "BK channel activation: structural and functional insights, *Trends Neurosci,* 2010, 33(9):415-423, which is incorporated herein by reference). In some embodiments, the peptide suppresses BK channel via modulation of the alpha subunit activity, rather than blocking the pore to prevent ion flow.

The agent may be a peptide of the invention, a nucleic acid encoding the peptide, or an expression construct comprising a nucleic acid encoding the peptide, wherein the condition is selected from among presbycusis, audiogenic seizures, alcohol addiction, cancer, and neurodegenerative disease. The agent may be contacted to the cell in a composition comprising the agent and a pharmaceutically acceptable carrier or diluent. Optionally, the composition may include other biologically active agents. As used herein, the term "contacting" in this context means bringing the agent into contact with the cell, or vice-versa, or any other manner of causing the agent and the cell to come into contact.

In some embodiments, the agent comprises a peptide of Table 1. In some embodiments, the peptide has an N-terminal and C-terminal disulfide bridge (i.e., a disulfide bridge between the cysteines). In some embodiments, the agent comprises a peptide comprising CRRGLVQVC (SEQ ID NO:3). In some embodiments, the agent comprises a peptide comprising an amino acid sequence consisting of CRR-GLVQVC (SEQ ID NO:3).

In the BK modulation method, the BK channel may be native to the cell or the BK channel may be heterologous to the cell. For example, the cell can be genetically modified to transiently or stably express a nucleic acid encoding a BK channel that is heterologous to the cell. In some embodiments, the cell is a human cell. In other embodiments, the cell is a non-human animal cell.

The invention also concerns cells comprising a nucleic acid encoding a peptide of the invention. The peptide may be native to the cell or the peptide may be heterologous to the cell. For example, the cell can be genetically modified to transiently or stably express a nucleic acid encoding a peptide. In some embodiments, the cell is a human cell. In other embodiments, the cell is a non-human animal cell. In some embodiments, the cell is a mammalian cell. In some embodiments, the cell is in isolated or purified form.

The peptides of the subject invention encompass those specifically exemplified herein, as well as any fragments and variants thereof that retain the desired biological activity. Typically, the desired biological activity will be modulation of BK channel function. In some embodiments, the BK channel activity is BKα channel function. In some embodiments, the peptide activity is suppression of the BK channel via modulation of the alpha subunit activity, as opposed to blocking the pore to prevent ion flow.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 5, 10, 15, 20, 25, 30, 35, 40, 50, 60, 70 or more amino acids added to, or removed from, either end of the disclosed peptides using standard techniques known in the art. In one embodiment, amino acids are removed from the N-terminus of a peptide of the invention. In a specific embodiment, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70 or more amino acids can, independently, be removed from either or both ends of a peptide of the invention. The skilled artisan, having the benefit of the teachings disclosed in the subject application, can determine whether a variant peptide retains the biological activity of the specific peptides exemplified herein.

Also within the scope of the subject invention are peptides which have the same amino acid sequences of a peptide exemplified herein except for amino acid substitutions, additions, or deletions within the sequence of the peptide, as long as these variant peptides retain substantially the same relevant biological activity as the peptides specifically exemplified herein. For example, conservative amino acid substitutions within a peptide which do not affect the ability of the peptide to, for example, modulation BK channel function would be within the scope of the subject invention. Thus, the peptides disclosed herein should be understood to include variants and fragments, as discussed above, of the specifically exemplified sequences.

The subject invention further includes nucleic acids (also referred to herein as polynucleotides) comprising nucleotide sequences which encode the peptides disclosed herein. In one embodiment, a polynucleotide comprises a nucleotide sequence which encodes a peptide comprising one or more of the amino acid sequences of Table 1, or a functional fragment or variant of the peptide. These nucleotide sequences can be readily constructed by those skilled in the art having the knowledge of the protein and peptide amino acid sequences which are presented herein. As would be appreciated by one skilled in the art, the degeneracy of the genetic code enables the artisan to construct a variety of nucleotide sequences that encode a particular peptide or protein. The choice of a particular nucleotide sequence could depend, for example, upon the codon usage of a particular expression system.

The subject invention contemplates the use of the peptides described herein in pharmaceutical compositions for administration to an animal or human subject for the treatment of conditions selected from among presbycusis, audiogenic seizures, alcohol addiction, cancer, and neurodegenerative disease. The peptides of the subject invention can be prepared in pharmaceutically acceptable carriers or diluents for administration to humans or animals in a physiologically tolerable form. Materials and methods for preparing such compositions are known in the art.

The peptides of the subject invention can be administered using a variety of techniques that are known in the art. In one embodiment, one or more peptides of the invention are administered as a topical preparation to the skin or an external membrane of a person or animal. The peptides can be encapsulated in liposomes that are targeted to specific cells or tissues and the liposome-encapsulated peptides delivered to the cells or tissue either in vitro, in vivo, or ex vivo. Procedures for preparing liposomes and encapsulating compounds within the liposome are well known in the art. See, for example, U.S. Pat. No. 5,252,348, which issued to Schreier et al. Peptides can also be conjugated or attached to other molecules, such as an antibody, that targeted a specific cell or tissue. Peptides can also be administered using a drug delivery system similar to that described in U.S. Pat. No. 4,625,014, which issued to Senter et al.

A further aspect of the claimed invention is the use of the claimed peptides to produce antibodies, both polyclonal and monoclonal. These antibodies can be produced using standard procedures well known to those skilled in the art. These antibodies may be used as diagnostic and therapeutic reagents. For example, interfering antibodies that bind to the peptide can be used as an antagonist to block the function of the peptide. Antibodies that are reactive with the peptides of the subject invention can also be used to purify the peptides from a crude mixture.

An antibody that is contemplated by the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$—$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the subject invention can be genus or species specific to a target. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975). Antibodies of the invention can be mammalian antibodies, including mouse, rat, goat, rabbit, pig, dog, cat, monkey, chimpanzee, ape, or human.

The subject invention also concerns compositions comprising one or more peptides or polynucleotides of the invention. In one embodiment, a composition further comprises a suitable carrier, diluent, or buffer. Compositions contemplated within the scope of the invention can comprise one or more peptides or polynucleotides of the invention and, optionally, one or more other compounds for treating the condition to be treated, e.g., presbycusis, audiogenic seizures, alcohol addiction, cancer, and neurodegenerative disease. In one embodiment, the composition comprises a peptide or polynucleotide of the invention in a pharmaceutically or physiologically acceptable carrier, buffer, or diluent.

In one embodiment, peptides, polynucleotides, antibodies, and other agents of the invention are modified so as to enhance uptake into a cell. In one embodiment, a lipophilic group is attached to a peptide, polynucleotide, or other agent of the invention. In one embodiment, a palmitic acid is attached to a peptide of the invention. In a specific embodiment, a palmitoyl-lysine group is attached to the peptide, for example at the N-terminus of the peptide. Other methods for enhancing uptake of a peptide, polynucleotide, and antibody into a cell are known in the art and are contemplated within the scope of the invention.

Peptides, polynucleotides, antibodies, compositions, and other agents of the invention can also be delivered into cells by encapsulation of the peptide, polynucleotide, antibody, and other agents of the invention within a liposome. Methods for encapsulation of peptides, polynucleotides, antibodies, and other agents of the invention within liposomes are well known in the art.

Peptides having substitution of amino acids other than those specifically exemplified in the subject peptides are also contemplated within the scope of the present invention. For example, non-natural amino acids can be substituted for the amino acids of a peptide of the invention, so long as the peptide having substituted amino acids retains substantially the same activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide having an amino acid of one class is replaced with another amino acid of the same class fall within the scope of the subject invention so long as the peptide having the substitution still retains substantially the same biological activity as a peptide that does not have the substitution. Table 2 below provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |

TABLE 2-continued

| Class of Amino Acid | Examples of Amino Acids |
|---|---|
| Uncharged Polar | Gly, Ser, Thr, Cys, Tyr, Asn, Gln |
| Acidic | Asp, Glu |
| Basic | Lys, Arg, His |

Single letter amino acid abbreviations are defined in Table 3.

TABLE 3

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The peptides of the present invention can be formulated into pharmaceutically-acceptable salt forms. Pharmaceutically-acceptable salts of the peptides of the invention can be prepared using conventional techniques. "Pharmaceutically acceptable salt" includes both acid and base addition salts. A pharmaceutically acceptable salt of any one of the peptides described herein is intended to encompass any and all pharmaceutically suitable salt forms. Preferred pharmaceutically acceptable salts described herein are pharmaceutically acceptable acid addition salts and pharmaceutically acceptable base addition salts. In some embodiments, the pharmaceutically acceptable salt comprises acetate, chloride, or trifluoroacetic acid (TFA) salt.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The subject invention also concerns polynucleotide expression constructs that comprise a nucleic acid of the present invention comprising a nucleotide sequence encoding a peptide of the present invention. In one embodiment, the polynucleotide encodes a peptide comprising the amino acid sequence CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a fragment or variant thereof that exhibits substantially the same activity as the full-length non-variant peptide. In some embodiments, the peptide is a circular peptide. In some embodiments, the peptide has an N-terminal and C-terminal disulfide bridge (i.e., a disulfide bridge between the cysteines).

In one embodiment, the polynucleotide encodes a peptide comprising an amino acid sequence consisting of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), or CSEWPQNVC (SEQ ID NO:26). In some embodiments, the peptide is a circular peptide. In some embodiments, the peptide has an N-terminal and C-terminal disulfide bridge (i.e., a disulfide bridge between the cysteines).

In some embodiments, the polynucleotide encodes a peptide comprising an amino acid sequence comprising any one of SEQ ID NO:27-61. In some embodiments, polynucleotide encodes a peptide comprising an amino acid sequence consisting of any one of SEQ ID NO:27-61 (including no further amino acid residues). In some embodiments, polynucleotide encodes a peptide consisting of an amino acid sequence consisting of any one of SEQ ID NO:27-61. In some embodiments, the peptide is a circular peptide. In some embodiments, the peptide has an N-terminal and C-terminal disulfide bridge (i.e., a disulfide bridge between the cysteines).

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in human or animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, viral and non-viral vectors, and other expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Feigner et al., 1987, *Proc Natl Acad Sci U.S.A.* 84(21):7413-7417). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides and peptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and)(BLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and)(BLAST) can be used. See NCBI/NIH website.

The subject invention also contemplates those polynucleotide molecules (encoding peptides of the invention) having sequences which are sufficiently homologous with the polynucleotide sequences encoding a peptide of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

$$Tm=81.5C+16.6 \ Log[Na+]+0.41(\% \ G+C)-0.61(\% \ formamide)-600/length \ of \ duplex \ in \ base \ pairs.$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

As used herein, the terms "nucleic acid", "polynucleotide", and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a peptide of the invention. The polynucleotide includes both the sense and antisense strands as either individual strands or in the duplex.

The subject invention also concerns a method for modulating BK channel activity in a cell having a BK channel in vitro or in vivo. In some embodiments, the BK channel activity is BK alpha subunit (BKα) channel function.

In one embodiment, a cell is contacted with an effective amount of one or more peptide, polypeptide construct, polynucleotide, or a composition of the invention. In one embodiment, the peptide has the amino acid sequence of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a fragment or variant thereof that exhibits BK channel modulatory activity (e.g., modulation of BKα channel function). In some embodiments, the peptide has an N-terminal and C-terminal disulfide bridge (i.e., a disulfide bridge between the cysteines). In some embodiments, the peptide comprises an amino acid sequence consisting of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), or CSEWPQNVC (SEQ ID NO:26).

In some embodiments, the peptide comprises an amino acid sequence comprising any one of SEQ ID NO:27-61. In some embodiments, the peptide comprises an amino acid sequence consisting of any one of SEQ ID NO:27-61 (including no further amino acid residues). In some embodiments, the peptide consists of an amino acid sequence consisting of any one of SEQ ID NO:27-61.

In some embodiments, the peptide is a circular peptide. In some embodiments, the peptide has an N-terminal and C-terminal disulfide bridge (i.e., a disulfide bridge between the cysteines).

The cell can be a human or mammalian cell. In some embodiments, the cell is a neuron or inner ear cell. In some embodiments, the cell is the cell of an inner ear organ, which includes the inner ear hair cell and the outer ear hair cell. In some embodiments, the cell is a spiral ganglion neuron.

Peptides, polynucleotides, compositions, and/or other agents of the invention can be delivered to a cell either through direct contact of peptide, etc. with the cell or via a carrier means. Carrier means for delivering compositions to cells are known in the art and include encapsulating the composition in a liposome moiety, and attaching the peptide or polynucleotide to a protein or nucleic acid that is targeted for delivery to the target cell. Published U.S. Patent Application Nos. 20030032594 and 20020120100 disclose amino acid sequences that can be coupled to another peptide, protein, or nucleic acid and that allows the peptide, protein, or nucleic acid to be translocated across biological membranes. Published U.S. Patent Application No. 20020035243 also describes compositions for transporting biological moieties, such as peptides and proteins across cell membranes for intracellular delivery. Peptides can also be delivered using a polynucleotide that encodes a subject peptide. In one embodiment, the polynucleotide is delivered to the cell where it is taken up and the polynucleotide is transcribed into RNA and the RNA is translated into the encoded peptide. Methods of the invention can be conducted in vitro or in vivo.

Another aspect of the invention concerns a method for treating a condition in a subject in need thereof, comprising administering an agent of the invention to the subject. In one embodiment, the condition is age-related hearing loss (presbycusis). In a further embodiment, the condition is audiogenic seizures. In a further embodiment, the condition is alcohol addiction. In a further embodiment, the condition is cancer. In a further embodiment, the condition is neurodegenerative disease (e.g., Alzheimer's disease (AD), Parkinson's disease (PD), Huntington's disease). In one embodiment, an effective amount of the agent is administered to a subject having the condition and who is in need of treatment thereof. In another embodiment, the subject is a person or non-human animal at risk of developing the condition.

The agent may be a peptide of the invention, a nucleic acid encoding the peptide, or an expression construct comprising a nucleic acid encoding the peptide. The agent may be administered to the subject in a composition comprising the agent and a pharmaceutically acceptable carrier or diluent.

In one embodiment, the peptide has the amino acid sequence of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a fragment or variant thereof that exhibits BK channel modulatory activity (e.g., modulation of BKα channel function). In some embodiments, the peptide has an N-terminal and C-terminal disulfide bridge (i.e., a disulfide bridge between the cysteines). In some embodiments, the peptide comprises an amino acid sequence consisting of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), or CSEWPQNVC (SEQ ID NO:26). In some embodiments, the peptide has an N-terminal and C-terminal disulfide bridge (i.e., a disulfide bridge between the cysteines).

Methods of the invention can also further comprise administering one or more biological molecules, compounds or drugs useful for treating the condition. Such biological molecules, compounds or drugs can be administered prior to, in conjunction with, and/or subsequent to administration of a peptide, polynucleotide, and/or composition of the present invention. The subject can be a human or other mammal, such as a dog, cat, or horse, or other animals having the condition. Methods of the invention can optionally comprise identifying that a person or animal has or may develop a condition and is in need of treatment or prevention. Methods for administering and formulating peptides and polynucleotides for administration to a subject are known in the art, examples of which are described herein. Peptides, polynucleotides, and/or compositions of the invention can be delivered to a cell either through direct contact of peptide, polynucleotide, or composition with the cell or via a carrier means. In one embodiment, a peptide, polynucleotide, or composition of the invention comprises an attached group that enhances cellular uptake of the peptide. In one embodiment, the peptide, polynucleotide, or composition is attached to an antibody that binds to a targeted cell. In another embodiment, the peptide, polynucleotide, or composition is encapsulated in a liposome. Peptides can also be delivered using a polynucleotide that encodes a subject peptide. Any polynucleotide having a nucleotide sequence that encodes a peptide of the invention is contemplated within the scope of the invention. In one embodiment, the polynucleotide is delivered to the cell where it is taken up and the polynucleotide is transcribed into RNA and the RNA is translated into the encoded peptide.

The subject invention also concerns methods for treating an oncological disorder (e.g., cancer) in a subject. In one embodiment, an effective amount of one or more peptide, polynucleotide, or composition of the present invention is administered to a subject having an oncological disorder and who is in need of treatment thereof. The subject invention also concerns methods for inhibiting the growth of a cancer cell by contacting the cell in vitro or in vivo with an effective amount of a peptide, polynucleotide, or composition of the present invention.

In one embodiment, the peptide has an amino acid sequence specifically disclosed herein, such as in Table 1 (SEQ ID NO:1-26), SEQ ID NO:27, or a fragment or variant of such amino acid sequences that exhibits BK channel modulating activity. In some embodiments, the peptide has an N-terminal and C-terminal disulfide bridge (i.e., a disulfide bridge between the cysteines).

In some embodiments, the peptide comprises an amino acid sequence comprising or consisting of: CXRXXYRVC (SEQ ID NO:41), CXRGXXXVC (SEQ ID NO:42), CRRXXXXVC (SEQ ID NO:43), CRXXXXAVC (SEQ ID NO:44), CXXGRXAVC (SEQ ID NO:45), CXXGXLXVC (SEQ ID NO:46), CGMXXXXVC (SEQ ID NO:47), CXXXKRXVC (SEQ ID NO:48), CXQXXXGVC (SEQ ID NO:49), CDXMXXXVC (SEQ ID NO:50), CEQRXXXVC (SEQ ID NO:51), CXEQRXXVC (SEQ ID NO:52), CXXEQRXVC (SEQ ID NO:53), CXXXEQRVC (SEQ ID NO:54), CGRRXXXVC (SEQ ID NO:55), CXGRRXXVC (SEQ ID NO:56), CXXGRRXVC (SEQ ID NO:57), CXXXGRRVC (SEQ ID NO:58), CGGGGXXVC (SEQ ID NO:59), CXGGGGXVC (SEQ ID NO:60), or CXXGGGGVC (SEQ ID NO:61), wherein X is any natural or non-natural amino acid. In some embodiments, the peptide has an N-terminal and C-terminal disulfide bridge (i.e., a disulfide bridge between the cysteines).

Methods of the invention can also further comprise administering or contacting a cell with one or more compounds or biological molecules for treating an oncological disorder. Such compounds can be administered prior to, in conjunction with, and/or subsequent to administration of a peptide, polynucleotide, and/or composition of the present invention. Methods of the invention can optionally include identifying a subject who is or may be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating peptides, polynucleotides, or compositions of the invention for administration to a patient are known in the art, examples of which are described herein.

Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Kaposi's sarcoma, melanoma, mesothelioma, soft tissue sarcoma, pancreatic cancer, lung cancer, leukemia (hairy cell, acute lymphoblastic, acute myeloid, chronic lymphocytic, chronic myeloid, and other), and lymphoma (Hodgkin's and non-Hodgkin's), and follicular lymphoma, and multiple myeloma.

Examples of cancers that can be treated according to the present invention are listed in Table 4.

TABLE 4

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, Childhood |
| Astrocytoma, Childhood Cerebellar | |
| Astrocytoma, Childhood Cerebral | Intraocular Melanoma |
| Basal Cell Carcinoma | Islet Cell Carcinoma (Endocrine Pancreas) |
| Bile Duct Cancer, Extrahepatic | Kaposi's Sarcoma |
| Bladder Cancer | Kidney (Renal Cell) Cancer |
| Bladder Cancer, Childhood | Kidney Cancer, Childhood |
| Bone Cancer, Osteosarcoma/Malignant Fibrous Histiocytoma | Laryngeal Cancer |
| | Laryngeal Cancer, Childhood |
| Brain Stem Glioma, Childhood | Leukemia, Acute Lymphoblastic, Adult |
| Brain Tumor, Adult | Leukemia, Acute Lymphoblastic, Childhood |
| Brain Tumor, Brain Stem Glioma, Childhood | Leukemia, Acute Myeloid, Adult |
| | Leukemia, Acute Myeloid, Childhood |
| Brain Tumor, Cerebellar Astrocytoma, Childhood | Leukemia, Chronic Lymphocytic |
| | Leukemia, Chronic Myelogenous |
| Brain Tumor, Cerebral Astrocytoma/Malignant Glioma, | Leukemia, Hairy Cell |
| | Lip and Oral Cavity Cancer |

TABLE 4-continued

Examples of Cancer Types

Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenstrom's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood

TABLE 4-continued

Examples of Cancer Types

| | |
|---|---|
| Thymoma and Thymic Carcinoma | Salivary Gland Cancer |
| Thyroid Cancer | Salivary Gland Cancer, Childhood |
| Thyroid Cancer, Childhood | Sarcoma, Ewing's Family of Tumors |
| Transitional Cell Cancer of the Renal Pelvis and Ureter | Sarcoma, Kaposi's |
| | Sarcoma, Soft Tissue, Adult |
| Trophoblastic Tumor, Gestational | Sarcoma, Soft Tissue, Childhood |
| Unknown Primary Site, Carcinoma of, Adult | Sarcoma, Uterine |
| | Sezary Syndrome |
| Unknown Primary Site, Cancer of, Childhood | Skin Cancer (non-Melanoma) |
| | Skin Cancer, Childhood |
| Unusual Cancers of Childhood | |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

For the treatment of oncological disorders (cancers), the peptides, polynucleotides, and compositions of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the peptides, polynucleotides, and compositions of this invention. For example, the peptides, polynucleotides, and compositions of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anticancer drugs or antibodies, such as, for example, GLEEVEC (Novartis Pharmaceuticals Corporation) and HERCEPTIN (Genentech, Inc.), respectively. Peptides, polynucleotides, and compositions of the invention can be used in combination with proteasome inhibitors, including, but not limited to, Bortezomib, Carfilzomib, and Salinosporamide A. The subject invention also concerns methods for inhibiting the growth of a cancer cell by contacting the cell in vitro or in vivo with an effective amount of a peptide, polynucleotide, or composition of the present invention.

The methods of the present invention can be used with humans and non-human animals. The animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

In one embodiment, one or more of the peptides of the subject invention can be provided in the form of a multiple peptide construct. Such a construct can be designed so that multiple peptides are linked to each other by intervening moieties wherein the intervening moieties are subsequently cleaved or removed following administration of the multiple peptide construct to a subject. Methods for constructing multiple peptide constructs are known in the art. For example, peptides of the present invention can be provided in the form resembling a multiple antigenic peptide (MAP) construct. The preparation of MAP constructs has been described in Tam J P, 1988, *Biochemistry* 85:5409-5413. MAP constructs utilize a core matrix of lysine residues onto which multiple copies of an immunogen are synthesized. Multiple peptide constructs, each containing different peptides, can be prepared and administered in accordance with methods of the present invention. In another embodiment, a multiple peptide construct can be prepared by preparing the subject peptides having at least one metal chelating amino acid incorporated therein, preferably at the amino and/or carboxy terminal of the peptide as described, for example, in U.S. Pat. No. 5,763,585. The peptides are then contacted with a solid support having attached thereto a metal ion specific for the metal chelating amino acid of the peptide. A multiple peptide construct of the invention can provide multiple copies of the exact same peptide, including variants or fragments of a subject peptide, or copies of different peptides of the subject invention.

Therapeutic application of the subject peptides, polynucleotides, and compositions containing them, can be accomplished by any suitable therapeutic method and technique presently or prospectively known to those skilled in the art. The peptides, polynucleotides, and compositions can be administered by any suitable route known in the art including, for example, topical, oral, nasal, rectal, parenteral, subcutaneous, or intravascular (e.g., intravenous or intra-arterial) routes of administration. For example, the peptides, polynucleotides and compositions can be administered to the subject systemically or locally. For presbycusis, for example, the peptides, polynucleotides, and compositions can be administered systemically (e.g., intravascularly) or locally, such as at the site of the inner ear (inner ear cell, outer ear hair cell, supporting cell, spiral ganglion cell, etc.). Administration of the peptides, polynucleotides, and compositions of the invention can be continuous or at distinct intervals as can be readily determined by a person skilled in the art.

Agents and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive peptide or polynucleotide is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptide or polynucleotide of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The peptides, polynucleotides, and compositions of the subject invention can also be administered utilizing liposome technology, slow release capsules, implantable pumps, and biodegradable containers. These delivery methods can, advantageously, provide a uniform dosage over an extended period of time.

The subject peptides and polynucleotides can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides known in the art (see, for example, U.S. Pat. No. 4,179,337). The subject peptides and polynucleotides can also be modified to improve cell membrane permeability. In one embodiment, cell membrane permeability can be improved by attaching a lipophilic moiety, such as a steroid, to the peptide or polynucleotide. In another embodiment, peptides and polynucleotides of the invention comprise a cell-penetrating peptide (CPP). CPPs are typically short peptides that are highly cationic and typically include several arginine and/or lysine amino acids. CPPs can be classified as hydrophilic, amphiphilic, or periodic sequence. In one embodiment, a CPP is provided at the terminus of a peptide or polynucleotide.

The subject invention also concerns a packaged dosage formulation comprising in one or more containers at least one peptide, polynucleotide, and/or composition of the subject invention formulated in a pharmaceutically acceptable dosage. The package can contain discrete quantities of the dosage formulation, such as tablet, capsules, lozenge, and powders. The quantity of peptide and/or polynucleotide in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

The subject invention also concerns kits comprising one or more peptides, polynucleotides, compositions, compounds, or molecules of the present invention in one or more containers. In one embodiment, a kit contains a peptide, polynucleotide, and/or composition of the present invention. In a specific embodiment, a kit comprises a peptide comprising the amino acid sequence CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a fragment or variant of the peptide that exhibits substantially the same activity as the full-length non-variant peptide, such as BK channel modulatory activity (e.g., modulation of BKα channel function). In some embodiments, the peptide is a circular peptide. In some embodiments, the peptide has an N-terminal and C-terminal disulfide bridge (i.e., a disulfide bridge between the cysteines).

A kit of the invention can also comprise, in addition to a peptide, polynucleotide, and/or composition of the invention, one or more compounds, biological molecules, or drugs for treating presbycusis, audiogenic seizures, alcohol addiction, cancer, or neurodegenerative disease.

In one embodiment, a kit of the invention includes instructions or packaging materials that describe how to administer a peptide, polynucleotide, compositions, compounds, or molecules of the kit. Containers of the kit can be of any suitable material, e.g., glass, plastic, metal, etc., and of any suitable size, shape, or configuration. In one embodiment, a peptide, polynucleotide, compositions, compounds, or molecules of the invention is provided in the kit as a solid, such as a tablet, pill, or powder form. In another embodiment, a peptide, polynucleotide, compositions, compounds, or molecules of the invention is provided in the kit as a liquid or solution. In one embodiment, the kit comprises an ampoule or syringe containing a peptide, polynucleotide, compositions, compounds, or molecules of the invention in liquid or solution form.

The subject invention can be used in gene therapy to treat a condition (presbycusis, audiogenic seizures, alcohol addiction, cancer, or neurodegenerative disease) in a person or animal subject. In one embodiment, a polynucleotide of the invention is incorporated into a cell or cells of a person or animal subject, and the polynucleotide expressed in the cell to produce a peptide of the invention. In a specific embodiment, a cell is removed from the body of the person or animal, the polynucleotide is incorporated into the cell ex vivo, and the cell is then reintroduced back into the body of the person or animal and the polynucleotide expressed in the cell. In one embodiment, the polynucleotide is stably incorporated into the genome of the cell. In a specific embodiment, the polynucleotide is provided in an expression construct that provides for expression of the polynucleotide in the cell. In one embodiment, the peptide expressed in the cell is transported outside the cell and into the extracellular space of the person or animal.

Any methods of the subject invention can optionally include a step of identifying a person or animal who is or who may be in need of treatment or prevention of a condition prior to administration of the peptide, polynucleotide, or composition of the invention.

As used herein, the term "peptide of the invention" includes peptides comprising an amino acid sequence comprising any one of CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a functional fragment or variant of any of the foregoing. In some embodiments, the peptide of the invention comprises an amino acid sequence consisting of any one of SEQ ID NO:1-26 (including no further amino acid residues). In some embodiments, the peptide of the invention consists of an amino acid sequence consisting of any one of SEQ ID NO:1-26. In some embodiments, the peptide of the invention comprises an amino acid sequence comprising any one of SEQ ID NO:27-61. In some embodiments, the peptide of the invention comprises an amino acid sequence consisting of any one of SEQ ID NO:27-61 (including no further amino acid residues). In some embodiments, the peptide of the invention consists of an amino acid sequence consisting of any one of SEQ ID NO:27-61. In some embodiments, the peptide of the invention comprises or consists of an amino acid sequence of Table 1.

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a peptide" should be construed to cover both a singular cell or singular peptide and a plurality of cells and a plurality of peptides unless indicated otherwise or clearly contradicted by the context.

The term "isolated," when used as a modifier of a peptide or polynucleotide, means that the peptides or compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

As used herein, the term "administration" is intended to include, but is not limited to, the following delivery methods: topical, including topical delivery to the round window membrane of the cochlea, oral, parenteral, subcutaneous, transdermal, transbuccal, intravascular (e.g., intravenous or intra-arterial), intramuscular, subcutaneous, intranasal, and intra-ocular administration.

As used herein, the term "hearing loss" is intended to mean any reduction in a subject's ability to detect sound. Hearing loss is defined as a 10 decibel (dB) standard threshold shift or greater in hearing sensitivity for two of 6 frequencies ranging from 0.5-6.0 (0.5, 1, 2, 3, 4, and 6) kHz (cited in Dobie, R. A. (2005) Audiometric Threshold Shift Definitions: Simulations and Suggestions, Ear and Hearing 26(1) 62-77). Hearing loss can also be only high frequency, and in this case would be defined as 5 dB hearing loss at two adjacent high frequencies (2-6 kHz), or 10 dB at any frequency above 2 kHz. One example of hearing loss is age-related (or aging-related) hearing loss, which is the gradual onset of hearing loss with increasing age.

The term "prevention" or "preventing" in the context of conditions, such as presbycusis, audiogenic seizures, alcohol addiction, cancer, and neurodegenerative disease, encompasses preventing initial onset, preventing relapse, or delaying onset of the condition. In the context of hearing loss, specifically, it is intended to refer to a significant decrease is the loss of hearing sensitivity within the aforesaid frequency range, particularly at the high frequency range 4-6 kHz.

EXEMPLIFIED EMBODIMENTS

Examples of embodiments of the invention include, but are not limited to:

Embodiment 1

A peptide comprising an amino acid sequence selected from among: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), CSEWPQNVC (SEQ ID NO:26), or a functional fragment or variant of any of the foregoing.

Embodiment 2

The peptide of embodiment 1, wherein the peptide comprises CRRGLVQVC (SEQ ID NO:3).

Embodiment 3

The peptide of embodiment 1, wherein the peptide comprises an amino acid sequence consisting of CRRGLVQVC (SEQ ID NO:3).

Embodiment 4

The peptide of embodiment 1, wherein the peptide comprises an amino acid sequence comprising the formula CXXXXXXVC (SEQ ID NO:27), wherein X is any natural or non-natural amino acid.

Embodiment 5

The peptide of embodiment 1, wherein the peptide comprises an amino acid sequence consisting of the formula CXXXXXXVC (SEQ ID NO:27), wherein X is any natural or non-natural amino acid.

Embodiment 6

The peptide of embodiment 1, wherein the peptide comprises an amino acid sequence comprising any one of SEQ ID NO:28-61, wherein X is any natural or non-natural amino acid.

Embodiment 7

The peptide of embodiment 1, wherein the peptide comprises an amino acid sequence consisting of any one of SEQ ID NO:28-61, wherein X is any natural or non-natural amino acid.

Embodiment 8

The peptide of embodiment 1, wherein the peptide consists of an amino acid sequence consisting of any one of SEQ ID NO:28-61, wherein X is any natural or non-natural amino acid.

Embodiment 9

The peptide of embodiment 1, wherein the peptide comprises an amino acid sequence selected from among: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), and CSEWPQNVC (SEQ ID NO:26).

Embodiment 10

The peptide of embodiment 1, wherein the peptide comprises an amino acid sequence consisting of: CARGVYRVC (SEQ ID NO:1), CRVAHRAVC (SEQ ID NO:2), CRRGLVQVC (SEQ ID NO:3), CPPGRGAVC (SEQ ID NO:4), CGMTKRPVC (SEQ ID NO:5), CWKSRWYVC (SEQ ID NO:6), CERRMYRVC (SEQ ID NO:7), CRRAYEMVC (SEQ ID NO:8), CRRKRHAVC (SEQ ID NO:9), CAVGRLAVC (SEQ ID NO:10), CLQEQRGVC (SEQ ID NO:11), CRKQGRRVC (SEQ ID NO:12), CEGRRARVC (SEQ ID NO:13). CLDGKLDVC (SEQ ID NO:14), CGGGGSRVC (SEQ ID NO:15), CFTGGGGVC (SEQ ID NO:16), CVWVKRNVC (SEQ ID NO:17), CGMASSFVC (SEQ ID NO:18), CDTMEQRVC (SEQ ID NO:19), CGQQSPGVC (SEQ ID NO:20), CDEMNWWVC (SEQ ID NO:21), CTQAETRVC (SEQ ID NO:22), CPKPNNTVC (SEQ ID NO:23), CVRAPPSVC (SEQ ID NO:24), CQAREVLVC (SEQ ID NO:25), or CSEWPQNVC (SEQ ID NO:26).

Embodiment 11

The peptide of any preceding embodiment, wherein the peptide is a circular peptide.

Embodiment 12

The peptide of embodiment 11, wherein the peptide has a disulfide bridge between cysteines.

Embodiment 13

The peptide of any one of embodiments 1 to 12, further comprising a heterologous amino acid sequence, or other moiety, fused directly or indirectly to the amino acid sequence.

Embodiment 14

The peptide of embodiment 13, wherein the moiety comprises a detectable label.

Embodiment 15

A nucleic acid encoding a peptide of any one of embodiments 1 to 13.

Embodiment 16

An expression construct comprising the nucleic acid of embodiment 15.

Embodiment 17

A composition comprising a peptide of any one of embodiments 1 to 14, the nucleic acid of embodiment 15, or the expression construct of embodiment 16; and a pharmaceutically acceptable carrier or diluent.

Embodiment 18

A method for treating a condition in a subject in need thereof, comprising administering an agent to the subject, wherein the agent comprises: a peptide of any one of embodiments 1 to 13, the nucleic acid of embodiment 15, the expression construct of embodiment 16, or the composition of embodiment 17, and wherein the condition is selected from among presbycusis, audiogenic seizures, alcohol addiction, cancer, and neurodegenerative disease.

Embodiment 19

The method of embodiment 18, wherein the agent comprises a peptide comprising CRRGLVQVC (SEQ ID NO:3).

Embodiment 20

The method of embodiment 18, wherein the agent comprises a peptide comprising an amino acid sequence consisting of CRRGLVQVC (SEQ ID NO:3).

Embodiment 21

The method of embodiment 18 or 19, wherein the condition is presbycusis.

Embodiment 22

The method of any one of embodiments 18 to 21, wherein the subject has the condition at the time of said administering, and the agent is administered to the subject as therapy.

Embodiment 23

The method of any one of embodiments 18 to 22, wherein the subject does not have the condition at the time of said administering, and the agent is administered to the subject as prophylaxis.

Embodiment 24

The method of any one of embodiments 18 to 23, wherein the agent is administered to the subject by a route selected from the group consisting of intravascular (e.g., intravenous or intra-arterial), intramuscular, subcutaneous, oral, intranasal, intra-ocular, topical, and transdermal.

Embodiment 25

The method of any one of embodiments 18 to 24, wherein the subject is a human.

Embodiment 26

A method for modulating large conductance $Ca^{2+}$ activated $K^+$ (BK) channel activity in a cell having a BK channel in vitro or in vivo, comprising contacting the cell in vitro or in vivo with an agent that comprises a peptide of any one of embodiments 1 to 13, the nucleic acid of embodiment 15, the expression construct of embodiment 16, or the composition of embodiment 17.

Embodiment 27

The method of embodiment 26, wherein the BK channel is native to the cell.

Embodiment 28

The method of embodiment 26, wherein the BK channel is heterologous to the cell and the cell has been genetically modified to express the heterologous BK channel.

Embodiment 29

The method of embodiment 26, wherein the cell is a human cell.

Embodiment 30

A method of delivering a cargo moiety to the brain of a subject, through the blood-brain barrier (BBB), comprising administering a polypeptide construct to the subject, wherein the polypeptide construct comprises a peptide of any one of embodiments 1 to 13 conjugated to the cargo moiety.

Embodiment 31

The method of embodiment 30, wherein the cargo moiety comprises a detectable label.

Embodiment 32

The method of embodiment 30, wherein the cargo moiety comprises a nucleic acid.

Embodiment 33

A cell comprising a nucleic acid encoding a peptide of any one of embodiments 1 to 13.

Embodiment 34

The cell of embodiment 33, wherein the nucleic acid expressed to produce the peptide.

Embodiment 35

An antibody, or antibody fragment, that selectively binds to a peptide of any one of embodiments 1 to 13.

Materials and Methods

Peptide Selection and Synthesis.

A monovalent phagemid display library (library C, Mobitec) was sequentially panned against three sets of HEK293 cells (see below). For negative selection, cells expressed the human glycine receptor a1 (hGlyRα1, X52009) and the rat small conductance calcium-activated channel 2 (rSK2, U69882.1). For positive selection, cells expressed the human BKα channel ZERO isoform (NM_002238). The progress of the selection process was monitored after each panning round by titering and sequencing the phagemid DNA. With 6 randomized and 3 fixed amino acids, this library started with $3\times10^7$ unique sequences. LS3 was selected as one of the sequences expressing motifs that were enriched more than 1000 fold. LS3 was synthesized as a TFA salt at 98-99% purity verified by HPLC and MS analysis (Genscript, Piscataway, N.J.). Stocks were dissolved in water at 10 mM and aliquots were lyophilized and stored at −80° C. As a secondary determination of identity and purity, in-house LC/MS was performed on a single quadrupole Mass Spectrophotometer (Agilent 6130) interfaced with a HPLC with a diode-array (UV-vis) detector (Agilent 1200).

C. elegans Strains and Transgenics.

Worms were cultivated at 20° C. as described with OP50 bacteria[67]. Worms cultured on plates contaminated with fungi or other bacteria were excluded from this study. The reference wild-type strain was N2 Bristol. The reference slo-1(null) strain and background for transgenic strains was NM1968, harboring the previously characterized null allele, js379[29]. Multi-site gateway technology (Invitrogen) was used to construct plasmids. 2501 kb of the native slo-1 promoter (Pslo-1) and the traditional unc9-54 UTR were used in combination with slo-1a(cDNA)::mCherry for a rescue construct. To test rescue with the human BK channel, an hslo(ZERO isoform, cDNA)::mCherry version was constructed. The slo-1(+) and hslo(+) plasmids were injected at a concentration of 20 and 10 ng/µl, respectively. The co-injection reporter PCFJ90 (1.25 ng/µl) was used to ensure proper transformation of the arrays. As such, JPS345 carried vxEx345, an extrachromosomal array containing [Pslo-1::slo-1::mCherry::unc-54UTR,Pmyo-2::mCherry::unc-54UTR]. JPS340 carried vxEx345, an extrachromosomal array containing [Pslo-1::hslo::mCherry::unc-54UTR, Pmyo-2::mCherry::unc-54UTR].

C. elegans Behavioral Assays.

Age-matched day one adults were cleaned of bacteria by letting them crawl around on an unseeded plate and then moved into a puddle of NGM or peptide dissolved in NGM on another unseeded plate. NGM and peptide treatment groups were always run in tandem to control for behavioral variance. While much shorter than typical drug applications in C. elegans[68,69], brief application in liquid was chosen to avoid potential catabolic by-products of incubation on metabolically active E. coli. Higher LS3 concentrations were used to compensate. The puddle was refreshed 1-2 times as needed, but let to fully absorb into the agar by 30 minutes. After 30 minutes, crawl behavior was videoed (Flea2 camera, Point Grey Research, Canada; StreamPix 3, NorPix, Canada). Copper rings restricted movement to a proscribed area. The worms were tracked offline using custom macros (Image-Pro, MediaCybernetics, Rockville, Md.) for 1 minute to obtain crawl speed (cm/min). Group means±SEM for peptide-treated vs. vehicle-treated controls were compared at each concentration with Student's t-tests. Rescue analysis was completed with two-way ANOVA (SigmaPlot, San Jose, Calif.). Crawl speeds for the peptide treated groups were also normalized to the performance of yoked controls. Normalized group means±SEM were compared vs. slo-1 null performance by two-way ANOVA.

HEK Cell Maintenance and Transfection.

HEK293 cells (ATCC, Manassas, Va.) were grown according to standard procedures. Cells were cultured at 37° C. in a 5% CO2 atmosphere in Dulbecco's modified Eagle's medium with 1-glutamine, sodium pyruvate and 10% fetal bovine serum (Invitrogen). Cell lines were split with trypsin/EDTA in Hanks' balanced salt solution (Invitrogen) up to 25-30 cycles. For phage display, stable lines stably expressed rSK2 or hBKα ZERO isoform. Cells were transfected (Lipofectamine 2000, Invitrogen) with hGlyRα1 and used 48 hours later. For electrophysiological recordings, cells were transfected with the hBKα ZERO or STREX isoform. Enhanced green fluorescent protein (EGFP) was cotransfected as a marker. Electrophysiological recordings were made 16-72 h after transfection. Although the profile of BK channel composition varies from tissue to tissue, the ZERO BK channel splice variant is widely expressed, particularly in the nervous system, serving as a representative form for studying the modulation of BK channel gating.

Patch-Clamp Recordings.

Voltage-clamp recordings were performed at room temperature (22-24° C.) using an inside-out configuration on patches pulled from HEK293 cells. The extracellular solution contained the following (in mM): 2 KCl, 136 KOH, 20 Hepes, 2 $MgCl_2$, adjusted to pH 7.2 with $MeSO_3H$. In order to apply peptide to the extracellular surface, patch electrodes (7-20 MΩ in resistance) were tip filled with normal extracellular solution and backfilled with extracellular solution containing LS3. Enough normal extracellular solution was included to provide at least five minutes of peptide-free recording (determined by plotting $P_o$ vs. time). The intracellular solution (in the bath) contained the following (in mM): 6 KCl, 132 KOH, 20 Hepes, adjusted to pH 7.2 with $MeSO_3H$. To achieve 750 nM free $Ca^{2+}$, 4.17 mL of 1 M $CaCl_2$ and 5 mM EGTA were included, a ratio verified by measurement with a $Ca^{2+}$-sensitive electrode. Voltage-clamp recordings made with an Axopatch 200A amplifier and custom macros in IgorPro. Analysis was performed with QUB (www.qub.buffalo.edu), including $P_o$, mean open time and three component exponential fits to closed dwell times. Group means±SEM for post peptide measures were plotted relative to pre peptide values and compared with pre values via planned paired t-tests.

Receptor Binding Assay.

LS3 was screened against a comprehensive panel of CNS-based proteins. Detailed protocols can be found within the *US National Institute of Mental Health Psychoactive Drug Screening Program (NIMH PDSP) Assay Protocol Book (version II)*, by B. L. Roth, March 2013 (available at: pdsp.med.unc.edu/PDSP%20Protocols%20II%202013-03-28.pdf). Briefly, competition binding assays tested whether 10 microM LS3 significantly altered binding of known radioligands for 33 targets. Radioactivity in the presence of the LS3 (sample) was calculated with the following equation and expressed as a percent inhibition: % inhibition=(sample CPM−non-specific CPM)/Total CPM−non-specific CPM)× 100. Total binding was measured with no competing ligand. Non-specific binding was measured in the presence of reference compound. The % inhibition by LS3 was measured 4 times for each receptor. Less than 50% inhibition was considered insignificant as this suggests a Ki<10 microM.

Mouse Subjects.

Multi-channel recordings were acquired from young CBA/CaJ mice. CBA/CaJ mice were chosen because the loss of peripheral function is similar to humans, making them a good model for the study of presbycusis[70,73]. Founder breeding pairs were obtained from The Jackson Laboratory (Bar Harbor, Me.), bred within the facilities of the university vivarium, and housed 3-4 per cage with litter-mates in rodent micro-isolator cages (36.9×15.6×13.2 cm), on a 12/12 hour light/dark cycle with ad lib water and food pellets. The temperature was maintained near 25° C. Cages were changed weekly, and the mice were monitored for signs of distress several times throughout the day. Only nulliparous mice were used for experiments, while breeder mice were kept in separate cages. All procedures were preapproved by the University of South Florida Committee on Animal Resources and are consistent with US Federal and NIH guidelines under IACUC protocol #0245R.

Surgical Preparation.

The mice were initially anesthetized with an intraperitoneal (i.p.) injection of ketamine and xylazine (100 mg/kg and 10 mg/kg). After anesthesia was induced, the top of the animal's head and neck was then shaved of fur to prevent contamination of the incision site. The skin was cleaned with germicidal scrub, rinsed with 70% alcohol, and prepped with iodine. The skull was then exposed, 2% lidocaine was applied to the site of incision, and a small brass tube was secured to the skull surface along the sagittal suture at bregma with vet bond and adhered with dental cement. Mice were given a recovery period of 24-48 hours before beginning the experimental sessions.

Drug Administration.

The peptide was prepared from a 10 mM aqueous stock solution and diluted down to 10 µM. Topical administration of either peptide or paxilline consisted of direct application of 1 µL solution to the exposed surface of the inferior colliculus at concentration dosages of 10 µM or an i.p. injection at a dose of 10 which is 0.33 ng/mg body weight for a 30 g mouse. Fresh solutions were made prior to each experiment.

Auditory Brainstem Response Procedures.

ABR recordings were acquired after the mice were anesthetized with ketamine (120 mg/kg) and xylazine (10 mg/kg) i.p., and respiration was monitored throughout to determine when additional supplemental doses were needed. Body temperature was kept constant at 37° C. using a feedback controlled heating pad (Physitemp TCAT2-LV Controller, Clifton, N.J.). Stimuli and recordings were generated digitally and controlled using a TDT RZ6 Multi-I/O Processor and their BioSig/SigGen software. Acoustic signals were played through a multi-field (MF1) magnetic speaker (TDT, Alachua, Fla.) with a total harmonic distortion<=1% from 1 kHz to 50 kHz, centered 0° azimuth in regards to the animal at a distance of 10 cm from the ear pinna. Tone bursts were presented at frequencies of 6, 12, 16, 20, 24, and 36 kHz (3 ms duration, 1 ms rise/fall time, alternating polarity) at a rate of 29 per second, attenuated in 5 dB steps from 80 dB SPL to 15 dB below threshold or 5 dB SPL, whichever was lower. Threshold was determined by visual inspection as the lowest intensity level which produced a defined wave in both replicates. All signals were calibrated using a Larsen Davis preamplifier, model 2221, with a ¼" microphone and a Larson Davis CAL200 Precision Acoustic Calibrator (PCB Piezotronics, Inc., Depew, N.Y.). ABR recordings were acquired using a TDT RA4LI low-impedance digital headstage and RA4PA Medusa preamp with the active (noninverting) electrode inserted at the vertex, the reference (inverting) electrode below the left ear, and the ground electrode below the right ear. The responses were amplified (20×), filtered (300 Hz-3 kHz), and averaged using BioSig software and the System III hardware (TDT) data-acquisition system. A total of 256 tone burst signal and 150 GIN signal recordings were replicated for each acquisition, and muscle artifacts exceeding 7 uV were rejected from the averaged response. All recordings took place in a sound-proof booth lined with echo-attenuating acoustic foam. ABR waveforms were analyzed using a custom MatLab program that automatically determined peak latencies and amplitudes in combination with secondary verification by an experimenter blind to the treatment group.

Extracellular Recording Procedures.

The right IC was stereotaxically located[74] and exposed via a small (<1.0 mm) craniotomy. Prior to recording, chlorprothixene (Taractin®, 5-12 µl/g i.m.) was administered. The animal was then secured in a custom stereotaxic frame (Newport-Klinger) that was located in a heated (34° C.) chamber lined with sound-absorbing foam (Sonex®). Multi-unit extracellular activity was recorded using vertically oriented single shank silicon acute penetrating 16-channel electrodes with an impedance ranging from 1.2 to 2.1 MΩ (Type-A, 3 mm×100 µm; NeuroNexus Technologies). The electrode was positioned stereotaxically over the IC after reference to the lambda landmark on the skull, and was advanced dorsoventrally into the IC by a micro positioner (Newport-Klinger PMC 100). The output from the electrode was attached to a low noise (5-6 uV noise floor) preamplifier (RA16), having an operating range of ±7 mV. Neural events were acquired and visualized in real-time using the OpenEx software platform (TDT, Inc.) and a custom designed MATLAB® (The MathWorks, Inc., Matick, Mass.) graphical interface. Neural recordings from each channel were then filtered (300-3000 Hz), amplified, and sampled at 25 kHz in a 1.25 ms time window subsequent to the event crossing a voltage discriminator. A spike triggering threshold of 4:1 signal to noise ratio (SNR) was automatically set for all channels. The search signal used to estimate the spike triggering thresholds was a 50-ms broadband noise stimulus presented at 60 dB SPL at a rate of 5/s. Each penetration typically yielded 8-16 active channels. Recording sessions lasted an average of 6-8 hours, and if at any time a mouse showed signs of discomfort, like excessive movement, it was removed from the apparatus and testing was halted.

Stimulus generation and presentation. Noise and tone bursts were generated digitally (Real-time Processor Visual Design Studio (RVPds), TDT) using a System 3 processor and D/A converter (TDT RX6) with 200 kHz sampling rate. The signals were routed to an electrostatic speaker (TDT ES1) with a flat frequency response from 4 to 110 kHz. This speaker was placed at 60° azimuth contralateral to the recording site. Harmonic distortions were measured with a Dynamic Signal Analyzer (HP 35665A) and were at least 60 dB below the primary signal. The distance between the speaker and the pinna was fixed at 22.5 cm and calibrated using a B&K 2610 amplifier and a ¼" microphone placed at the location of the pinna. eRFs from all active channel were acquired simultaneously using 25 ms (5 ms rise/fall) tone burst stimuli presented from 0 to 90 dB SPL in 5 dB steps and from 2 to 64 kHz for a total of 2125 frequency and intensity combinations that were presented pseudo-randomly five times at a rate of 10/s.

Spike Sorting.

Spike waveforms were processed in MATLAB® using the TDT OpenDeveloper ActiveX controls and passed to AutoClass C v3.3.4, an unsupervised Bayesian classification system that seeks a maximum posterior probability classification, developed at the NASA Ames Research Center[75,76]. AutoClass scans the dataset of voltage-time waveforms according to custom specified spike parameters to produce the best fit classifications of the data, which may include distinct single- and multi-unit events, as well as noise. To discriminate the signal from noise in the present study, the variance of the background noise was estimated as the quartile range of the first five digitization points of the spike waveform, at these are recorded prior to the threshold-crossing event. To avoid overloading AutoClass with excessive noise, which leads to over-classification, this noise measure is used to screen the event waveform data, such that only voltage points with absolute values greater than this noise floor were presented for use in the classification. Once the classes had been determined in each channel of data, they were visualized within a custom MATLAB® program and assigned to multi-unit, single-unit, or noise classes. Event classes which were categorized as noise were subsequently discarded, and units with distinct biphasic waveforms and good SNR were classified as single-units. As most channels recorded information elicited from the spiking of two or more neurons, all recordings units in this paper were considered to be MUA[77]. Nonetheless, there was no observation of any consistent differences in the RFs between single units and multi-unit clusters.

Data Analyses.

FRAs were analyzed using a custom MATLAB® program We classified RF tuning using a method similar to that used to classify neurons in the primary AC[78]. The frequency at which driven activity is responsive at the lowest intensity (threshold) is classified as the characteristic frequency (CF) and the point in the receptive field, which elicits the maximal driven activity is categorized as the best frequency (BF). A custom MATLAB® program was used to calculate the edges of each eRF, and this was verified via visual inspection to ensure no non-driven activity was included in the calculation. The edges of the RF were defined, in 10 dB steps above threshold, as the activity levels that were equal to or greater than the background rate and at least 15% of the maximum rate. Each RF was categorized into low-BF (<15 kHz), mid-BF (15-30 kHz), and high-BF (>30 kHz) groups based on the topographical representation proposed by Willott[79]. The maximum driven rate, as well as the total spike counts, were taken from the baseline.

Statistical analysis and graphs were created using Graph-Pad Prism version 6.01 for Windows (GraphPad Software, La Jolla, Calif.). The majority of the data results are presented using box plots, which allows for both mean, along with the ±standard error of the mean (SEM) and median values to be denoted. A one-way ANOVA test and Tukey's repeated measures analysis procedure were used to evaluate the effects of the peptide on the spike counts within the baseline eRF. Alpha was set at 0.05 for all statistical tests.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—LS3 Peptide Suppresses BK Channel Activity and Decreases Spontaneous and Sound-Evoked Activity of Inferior Colliculus Neurons The inventors propose that BK channel-directed peptides can be used to increase temporal precision and/or gain in central auditory processing in order to alleviate some of the deficits caused by age-related hearing loss.

The inventors have identified a novel BK channel directed peptide (LS3; SEQ ID NO:3) that suppresses BK channel via modulation of the alpha subunit activity, rather than blocking the pore to prevent ion flow. This peptide is 9 amino acids in length (sequence: CRRGLVQVC; SEQ ID NO:3) with an N- and C-terminal disulfide bridge. Application of this peptide at 500 pM-500 nM to BK channels expressed in HEK293 cells causes a strong suppression of channel openings (by ~⅔rds at 60 mV). Little to no suppression is seen when applied at 50 pM, indicating an IC50 in the low hundreds of pM range.

To provide a measure of whether the peptide modulates BK channel function specifically, the inventors tested the peptide for the ability to alter a BK channel-mediated behavior in *Caenorhabditis elegans*. *C. elegans* express a wide variety of highly conserved potassium channels, in addition to about two-thirds of all mammalian proteins. The BK channel is highly conserved between worms and mammals. This assay revealed that the peptide reduces crawl speed in wild-type but not BK channel-null worms. Moreover, the reduction in crawl speed can be rescued in the BK channel-null worms with expression of either the wild-type worm BK channel or the wild-type human BK channel. These data indicate that the peptide acts with a high level of specificity at both the nematode and mammalian BK channel.

This novel BK channel modulating peptide shows the ability to cross the mammalian blood-brain barrier as well as alter neuronal activity in vivo. When applied to the surface of the dura in mouse, this peptide alters neuronal properties of inferior colliculus neurons after about 10 minutes, showing that the peptide can cross the blood-brain barrier (BBB). To further demonstrate that the peptide can cross the blood-brain barrier (BBB), the inventors attached a fluorophore to the peptide. When this compound was applied to the dura, fluorescence could be seen at ~1200 microns in depth after 8 hours. This indicates that not only can the peptide cross the BBB, but it can also port other molecules across as well.

Once across the blood-brain barrier, the peptide shows a concentration-dependent effect on sound-evoked activity among inferior colliculus neurons. When applied at 10 microM (2 uL), the peptide decreases spontaneous and sound-evoked activity of inferior colliculus neurons by suppressing pre-synaptic input for neurons of the central nucleus of the inferior colliculus. These results vary among the tonotopic regions of the inferior colliculus with the most robust decreases seen in the most ventral locations. This suppression of activity is similar to the strong suppression of activity seen with a known BK channel blocker, paxilline. These similarities between the effect of peptide and paxilline suggest that the peptide is altering inferior colliculus neuronal properties through a BK channel-mediated mechanism.

In contrast, when applied at 1 microM, the pre-synaptic suppression appears to be reduced enough to reveal interesting post-synaptic modifications. This is particularly true for dorsal units, for which the pre-synaptic suppression of activity is less. At this concentration, the peptide lowers sound-evoked thresholds and provides better definition to neuronal receptive fields in aged mice. The peptide also suppresses spontaneous activity. This improvement in sound-evoked thresholds and receptive field definition in aged mice is clinically relevant to the improvement of age-related hearing loss.

This peptide resulted from a screen that yielded other BK channel modulating peptides as well. These peptides are all 9 amino acids in length with a C-to-N terminal disulfide bond. Some of the other peptides share motifs with the peptide discussed above. Putatively, these motifs share functional qualities. For example, both this and another peptide (LS1), which share some but not all motifs, are able to modulate phosphorylation at a specific site on the BK channel. Data suggests that LS1 also is able to cross the blood-brain barrier and alter neuronal properties in vivo in a similar manner to the peptide discussed above. Pre-synaptic suppression of activity is not as strong for LS1 as LS3, which may prove to be advantageous. Results are shown in the Figures. Scott L L et al., "A novel BK channel-targeted peptide suppresses sound evoked activity in the mouse inferior colliculus," *Sci Rep*, 2017 Feb. 14, 7:42433, is incorporated herein by reference in its entirety, including all Figures and Results.

The present inventors have identified a cohort of peptides that modulate the large conductance calcium-activated potassium channel. One well-characterized peptide, LS3, reduces opening of the BK channel. The BK channel is gated both by voltage and intracellular calcium. It is widely expressed in human tissue where it regulates smooth muscle tone, endocrine secretion and neuronal excitability. While widely expressed, global knockdown of the constitutive pore-forming a subunit or regulatory subunits is not lethal.

The BK channel is considered a promising pharmacological target for a broad range of diseases. As outlined above, the peptide LS3 shows promise for treating age-related hearing loss. This peptide and others in the cohort have other potential uses as well. Our data most obviously points to an additional use in treating epilepsy. A BK channel gain-of-function mutation is associated with an increased risk for epilepsy in humans and animal models. Pharmacological treatment with a BK channel blocker is effective in some in vivo and in vitro seizure models. More specifically, a BK channel blocker can reduce audiogenic seizure activity in a mouse epilepsy model. The inferior colliculus is a critical site for the initiation of audiogenic seizures. The action of LS3 as a BK channel closer predicts similar activity in epilepsy models to known BK channel blockers. The reduction in activity in the inferior colliculus, as shown at the higher dose, specifically predicts a protective action against audiogenic seizures.

There is also evidence that LS3 and other peptides in this cohort (Table 1) may be useful in addressing alcohol addiction. In *Caenorhabditis elegans* and *Drosophila*, null mutations in the highly conserved invertebrate BKα channels restrict acute ethanol intoxication and tolerance. These invertebrates are intoxicated by similar internal concentrations of alcohol as mammals and likely share similar mechanisms of intoxication, tolerance and other alcohol-related behaviors. LS3 and another peptide in this cohort reduce acute alcohol intoxication in *C. elegans*. Other peptides in this cohort also reduce behavioral symptoms of withdrawal from chronic alcohol exposure in *C. elegans*. The inventors propose that these peptides would influence alcohol behaviors in mammals.

LS3 may also have therapeutic value in treating cancers. BK channels are expressed in human tumor cells where, in many cases, they support tumor growth and spreading. Antagonists stop tumor proliferation in vitro. A preliminary experiment suggests LS3 can disrupt cell proliferation.

In addition, the peptides may have therapeutic value in treating late-stage neurodegenerative diseases. BK channel blockers in the central nervous system (CNS) enhance synaptic transmission, potentially restoring some cognitive function in chronic neurodegenerative diseases (e.g., Alzheimer's disease (AD), Parkinson's disease (PD), Huntington's disease). Moreover, BK channel blockers can modulate microglia activation, which could be protective in later stages of these same chronic neurodegenerative diseases.

By virtue of their receptor binding ability, the peptides may also be used as tools for research and drug screening, for example, in competitive assays to identify and compare other agents that have receptor binding affinity. Optionally, the peptides may include a detectable label for use in this way.

LS3 could be used to modulate circadian rhythms. Changes in BK channel expression and composition in the suprachiasmatic nucleus (SCN) in turn alters circadian behavior and SCN neuronal firing rates. It is known that BK currents are larger during the night than during the day, and inactivation of the BK channel at night can switch SCN activity to daytime levels. LS3 is likely to provide similar regulation of SCN activity.

It is known that knockdown of the a subunit of the BK channel causes defects in motor performance, erectile dysfunction and over-active bladders in mouse. Experiments in ex vivo preparations of bladder suggest that LS3 does not show typical anti-BK channel activity in smooth muscle. This is fortuitous for reducing negative side effects in the above applications.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for treating presbycusis in a subject in need thereof, the method comprising: administering an effective amount of a peptide,
wherein the presbycusis is associated with aberrant neural activity that is modulated by large conductance Ca2+ activated K+ (BK) channel function in one or more cells of the subject; and
wherein the amino acid sequence of the peptide comprises CRRGLVQVC (SEQ ID NO:3), and wherein the peptide is a circular peptide having a disulfide bridge between cysteines.

2. The method of claim 1, wherein the peptide is administered to the subject by one or more routes selected from intravascular, intramuscular, subcutaneous, oral, intranasal, intra-ocular, topical, and transdermal.

3. The method of claim 2, wherein the subject is a human.

4. The method of claim 1, wherein the amino acid sequence of the peptide consists of: CRRGLVQVC (SEQ ID NO:3).

5. A method comprising:
modulating, in vitro, large conductance Ca2+ activated K+ (BK) channel activity in a mammalian cell having a BK channel, comprising contacting the cell with a peptide, wherein the amino acid sequence of the peptide comprises CRRGLVQVC (SEQ ID NO:3), wherein the peptide is a circular peptide having a disulfide bridge between cysteines.

6. The method of claim 5, wherein the peptide comprises a detectable label.

7. The method of claim 5, wherein the amino acid sequence of the peptide consists of CRRGLVQVC (SEQ ID NO:3).

8. A method for delivering a cargo moiety to the brain of a subject, through the blood-brain barrier (BBB), the method comprising: administering via a route selected from one or more of intravascular, intramuscular, subcutaneous, oral, intranasal, intra-ocular, topical, and transdermal, an effective amount of a polypeptide construct to the subject, thereby delivering the cargo moiety to the brain of the subject, wherein the polypeptide construct comprises a peptide conjugated to the cargo moiety;
wherein the amino acid sequence of the peptide comprises: CRRGLVQVC (SEQ ID NO:3), wherein the peptide is a circular peptide having a disulfide bridge between cysteines;
wherein the peptide and the cargo are delivered to the brain of the subject.

9. The method of claim 8, wherein the cargo moiety comprises a detectable label.

10. The method of claim 8, wherein the amino acid sequence of the peptide consists of CRRGLVQVC (SEQ ID NO: 3).

* * * * *

UNITED STATES PATENT AND TRADEMARK OFFICE
CERTIFICATE OF CORRECTION

Page 1 of 1

PATENT NO.        : 11,214,595 B2
APPLICATION NO.   : 16/222534
DATED             : January 4, 2022
INVENTOR(S)       : Luisa Lynn Scot et al.

It is certified that error appears in the above-identified patent and that said Letters Patent is hereby corrected as shown below:

In the Specification

Column 1, Line 51, "pore-forming a subunit" should read --pore-forming α subunit--.

Column 6, Line 28, "hGlyRa1" should read --hGlyRα1--.

Column 31, Line 32, "Feigner" should read --Felgner--.

Column 31, Line 56, "and)(BLAST" should read --and XBLAST--.

Column 31, Line 64, "and)(BLAST" should read --and XBLAST--.

Column 48, Line 46, "receptor a1" should read --receptor α1--.

Column 50, Line 43, "prebycusis$^{70,73}$" should read --prebycusis$^{70-73}$--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 61

<210> SEQ ID NO 1
<211> LENGTH: 9
<212> TYPE: PRT
<213> ORGANISM: Artificial
<220> FEATURE:
<223> OTHER INFORMATION: pskan1/LS1 peptide

<400> SEQUENCE: 1

Cys Ala Arg Gly Val Tyr Arg Val Cys
1               5

<210> SEQ ID NO 2
<211> LENGTH: 9
<212> TYPE: PRT
<213> ORGANISM: Artificial
<220> FEATURE:
<223> OTHER INFORMATION: pskan2/LS2 peptide

<400> SEQUENCE: 2

Cys Arg Val Ala His Arg Ala Val Cys
1               5
```

```
<210> SEQ ID NO 3
<211> LENGTH: 9
<212> TYPE: PRT
<213> ORGANISM: Artificial
<220> FEATURE:
<223> OTHER INFORMATION: pskan3/LS3 peptide

<400> SEQUENCE: 3

Cys Arg Arg Gly Leu Val Gln Val Cys
1               5

<210> SEQ ID NO 4
<211> LENGTH: 9
<212> TYPE: PRT
<213> ORGANISM: Artificial
<220> FEATURE:
<223> OTHER INFORMATION: pskan4/LS4 peptide

<400> SEQUENCE: 4

Cys Pro Pro Gly Arg Gly Ala Val Cys
1               5

<210> SEQ ID NO 5
<211> LENGTH: 9
<212> TYPE: PRT
<213> ORGANISM: Artificial
<220> FEATURE:
<223> OTHER INFORMATION: pskan5/LS5 peptide

<400> SEQUENCE: 5

Cys Gly Met Thr Lys Arg Pro Val Cys
1               5

<210> SEQ ID NO 6
<211> LENGTH: 9
<212> TYPE: PRT
<213> ORGANISM: Artificial
<220> FEATURE:
<223> OTHER INFORMATION: pskan21/LS6 peptide

<400> SEQUENCE: 6

Cys Asp Glu Met Asn Trp Trp Val Cys
1               5

<210> SEQ ID NO 7
<211> LENGTH: 9
<212> TYPE: PRT
<213> ORGANISM: Artificial
<220> FEATURE:
<223> OTHER INFORMATION: pskan7/LS7 peptide

<400> SEQUENCE: 7

Cys Glu Arg Arg Met Tyr Arg Val Cys
1               5

<210> SEQ ID NO 8
<211> LENGTH: 9
<212> TYPE: PRT
<213> ORGANISM: Artificial
<220> FEATURE:
<223> OTHER INFORMATION: pskan8/LS8 peptide

<400> SEQUENCE: 8

Cys Arg Arg Ala Tyr Glu Met Val Cys
1               5
```

```
<210> SEQ ID NO 9
<211> LENGTH: 9
<212> TYPE: PRT
<213> ORGANISM: Artificial
<220> FEATURE:
<223> OTHER INFORMATION: pskan9/LS9 peptide

<400> SEQUENCE: 9

Cys Arg Arg Lys Arg His Ala Val Cys
1               5

<210> SEQ ID NO 10
<211> LENGTH: 9
<212> TYPE: PRT
<213> ORGANISM: Artificial
<220> FEATURE:
<223> OTHER INFORMATION: pskan10/LS10 peptide

<400> SEQUENCE: 10

Cys Ala Val Gly Arg Leu Ala Val Cys
1               5

<210> SEQ ID NO 11
<211> LENGTH: 9
<212> TYPE: PRT
<213> ORGANISM: Artificial
<220> FEATURE:
<223> OTHER INFORMATION: pskan11/LS11 peptide

<400> SEQUENCE: 11

Cys Leu Gln Glu Gln Arg Gly Val Cys
1               5

<210> SEQ ID NO 12
<211> LENGTH: 9
<212> TYPE: PRT
<213> ORGANISM: Artificial
<220> FEATURE:
<223> OTHER INFORMATION: pskan12/LS12 peptide

<400> SEQUENCE: 12

Cys Arg Lys Gln Gly Arg Arg Val Cys
1               5

<210> SEQ ID NO 13
<211> LENGTH: 9
<212> TYPE: PRT
<213> ORGANISM: Artificial
<220> FEATURE:
<223> OTHER INFORMATION: pskan13/LS13 peptide

<400> SEQUENCE: 13

Cys Glu Gly Arg Arg Ala Arg Val Cys
1               5

<210> SEQ ID NO 14
<211> LENGTH: 9
<212> TYPE: PRT
<213> ORGANISM: Artificial
<220> FEATURE:
<223> OTHER INFORMATION: pskan14/LS14 peptide

<400> SEQUENCE: 14

Cys Leu Asp Gly Lys Leu Asp Val Cys
1               5
```

```
<210> SEQ ID NO 15
<211> LENGTH: 9
<212> TYPE: PRT
<213> ORGANISM: Artificial
<220> FEATURE:
<223> OTHER INFORMATION: pskan15/LS15 peptide

<400> SEQUENCE: 15

Cys Gly Gly Gly Gly Ser Arg Val Cys
1               5

<210> SEQ ID NO 16
<211> LENGTH: 9
<212> TYPE: PRT
<213> ORGANISM: Artificial
<220> FEATURE:
<223> OTHER INFORMATION: pskan16/LS16 peptide

<400> SEQUENCE: 16

Cys Phe Thr Gly Gly Gly Gly Val Cys
1               5

<210> SEQ ID NO 17
<211> LENGTH: 9
<212> TYPE: PRT
<213> ORGANISM: Artificial
<220> FEATURE:
<223> OTHER INFORMATION: pskan17/LS17 peptide

<400> SEQUENCE: 17

Cys Val Trp Val Lys Arg Asn Val Cys
1               5

<210> SEQ ID NO 18
<211> LENGTH: 9
<212> TYPE: PRT
<213> ORGANISM: Artificial
<220> FEATURE:
<223> OTHER INFORMATION: pskan18/LS18 peptide

<400> SEQUENCE: 18

Cys Gly Met Ala Ser Ser Phe Val Cys
1               5

<210> SEQ ID NO 19
<211> LENGTH: 9
<212> TYPE: PRT
<213> ORGANISM: Artificial
<220> FEATURE:
<223> OTHER INFORMATION: pskan19/LS19 peptide

<400> SEQUENCE: 19

Cys Asp Thr Met Glu Gln Arg Val Cys
1               5

<210> SEQ ID NO 20
<211> LENGTH: 9
<212> TYPE: PRT
<213> ORGANISM: Artificial
<220> FEATURE:
<223> OTHER INFORMATION: pskan20/LS20 peptide

<400> SEQUENCE: 20

Cys Gly Gln Gln Ser Pro Gly Val Cys
1               5

<210> SEQ ID NO 21
```

```
<211> LENGTH: 9
<212> TYPE: PRT
<213> ORGANISM: Artificial
<220> FEATURE:
<223> OTHER INFORMATION: pskan6 peptide

<400> SEQUENCE: 21

Cys Trp Lys Ser Arg Trp Tyr Val Cys
1               5

<210> SEQ ID NO 22
<211> LENGTH: 9
<212> TYPE: PRT
<213> ORGANISM: Artificial
<220> FEATURE:
<223> OTHER INFORMATION: pskan22 peptide

<400> SEQUENCE: 22

Cys Thr Gln Ala Glu Thr Arg Val Cys
1               5

<210> SEQ ID NO 23
<211> LENGTH: 9
<212> TYPE: PRT
<213> ORGANISM: Artificial
<220> FEATURE:
<223> OTHER INFORMATION: pskan23 peptide

<400> SEQUENCE: 23

Cys Pro Lys Pro Asn Asn Thr Val Cys
1               5

<210> SEQ ID NO 24
<211> LENGTH: 9
<212> TYPE: PRT
<213> ORGANISM: Artificial
<220> FEATURE:
<223> OTHER INFORMATION: pskan24 peptide

<400> SEQUENCE: 24

Cys Val Arg Ala Pro Pro Ser Val Cys
1               5

<210> SEQ ID NO 25
<211> LENGTH: 9
<212> TYPE: PRT
<213> ORGANISM: Artificial
<220> FEATURE:
<223> OTHER INFORMATION: pskan25 peptide

<400> SEQUENCE: 25

Cys Gln Ala Arg Glu Val Leu Val Cys
1               5

<210> SEQ ID NO 26
<211> LENGTH: 9
<212> TYPE: PRT
<213> ORGANISM: Artificial
<220> FEATURE:
<223> OTHER INFORMATION: pskan26 peptide

<400> SEQUENCE: 26

Cys Ser Glu Trp Pro Gln Asn Val Cys
1               5

<210> SEQ ID NO 27
<211> LENGTH: 9
```

```
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(7)
<223> OTHER INFORMATION: Xaa can be any naturally occurring amino acid

<400> SEQUENCE: 27

Cys Xaa Xaa Xaa Xaa Xaa Xaa Val Cys
1               5

<210> SEQ ID NO 28
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 28

Xaa Arg Xaa Xaa Tyr Arg
1               5

<210> SEQ ID NO 29
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 29

Xaa Arg Gly Xaa Xaa Xaa
1               5

<210> SEQ ID NO 30
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (3)..(6)
<223> OTHER INFORMATION: Xaa can be any naturally occurring amino acid

<400> SEQUENCE: 30

Arg Arg Xaa Xaa Xaa Xaa
1               5

<210> SEQ ID NO 31
<211> LENGTH: 6
<212> TYPE: PRT
<213> ORGANISM: Artificial
<220> FEATURE:
```

```
<223> OTHER INFORMATION: enriched motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 31

Arg Xaa Xaa Xaa Xaa Ala
1               5

<210> SEQ ID NO 32
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Xaa Xaa Gly Arg Xaa Ala
1               5

<210> SEQ ID NO 33
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 33

Xaa Xaa Gly Xaa Leu Xaa
1               5

<210> SEQ ID NO 34
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (3)..(6)
<223> OTHER INFORMATION: Xaa can be any naturally occurring amino acid

<400> SEQUENCE: 34

Gly Met Xaa Xaa Xaa Xaa
1               5

<210> SEQ ID NO 35
<211> LENGTH: 6
<212> TYPE: PRT
<213> ORGANISM: Artificial
```

```
<220> FEATURE:
<223> OTHER INFORMATION: enriched motif
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 35

Xaa Xaa Xaa Lys Arg Xaa
1               5

<210> SEQ ID NO 36
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid

<400> SEQUENCE: 36

Xaa Gln Xaa Xaa Xaa Gly
1               5

<210> SEQ ID NO 37
<211> LENGTH: 6
<212> TYPE: PRT
<213> ORGANISM: Artificial
<220> FEATURE:
<223> OTHER INFORMATION: enriched motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 37

Asp Xaa Met Xaa Xaa Xaa
1               5

<210> SEQ ID NO 38
<211> LENGTH: 3
<212> TYPE: PRT
<213> ORGANISM: Artificial
<220> FEATURE:
<223> OTHER INFORMATION: enriched motif

<400> SEQUENCE: 38

Glu Gln Arg
1

<210> SEQ ID NO 39
<211> LENGTH: 3
<212> TYPE: PRT
<213> ORGANISM: Artificial
<220> FEATURE:
<223> OTHER INFORMATION: enriched motif
```

```
<400> SEQUENCE: 39

Gly Arg Arg
1

<210> SEQ ID NO 40
<211> LENGTH: 4
<212> TYPE: PRT
<213> ORGANISM: Artificial
<220> FEATURE:
<223> OTHER INFORMATION: enriched motif

<400> SEQUENCE: 40

Gly Gly Gly Gly
1

<210> SEQ ID NO 41
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 41

Cys Xaa Arg Xaa Xaa Tyr Arg Val Cys
1               5

<210> SEQ ID NO 42
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 42

Cys Xaa Arg Gly Xaa Xaa Xaa Val Cys
1               5

<210> SEQ ID NO 43
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (4)..(7)
<223> OTHER INFORMATION: Xaa can be any naturally occurring amino acid

<400> SEQUENCE: 43

Cys Arg Arg Xaa Xaa Xaa Xaa Val Cys
1               5

<210> SEQ ID NO 44
```

```
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (3)..(6)
<223> OTHER INFORMATION: Xaa can be any naturally occurring amino acid

<400> SEQUENCE: 44

Cys Arg Xaa Xaa Xaa Xaa Ala Val Cys
1               5

<210> SEQ ID NO 45
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 45

Cys Xaa Xaa Gly Arg Xaa Ala Val Cys
1               5

<210> SEQ ID NO 46
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 46

Cys Xaa Xaa Gly Xaa Leu Xaa Val Cys
1               5

<210> SEQ ID NO 47
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (4)..(7)
<223> OTHER INFORMATION: Xaa can be any naturally occurring amino acid

<400> SEQUENCE: 47

Cys Gly Met Xaa Xaa Xaa Xaa Val Cys
1               5
```

```
<210> SEQ ID NO 48
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 48

Cys Xaa Xaa Xaa Lys Arg Xaa Val Cys
1               5

<210> SEQ ID NO 49
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 49

Cys Xaa Gln Xaa Xaa Xaa Gly Val Cys
1               5

<210> SEQ ID NO 50
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 50

Cys Asp Xaa Met Xaa Xaa Xaa Val Cys
1               5

<210> SEQ ID NO 51
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (5)..(7)
<223> OTHER INFORMATION: Xaa can be any naturally occurring amino acid

<400> SEQUENCE: 51

Cys Glu Gln Arg Xaa Xaa Xaa Val Cys
1               5
```

```
<210> SEQ ID NO 52
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 52

Cys Xaa Glu Gln Arg Xaa Xaa Val Cys
1               5

<210> SEQ ID NO 53
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 53

Cys Xaa Xaa Glu Gln Arg Xaa Val Cys
1               5

<210> SEQ ID NO 54
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(4)
<223> OTHER INFORMATION: Xaa can be any naturally occurring amino acid

<400> SEQUENCE: 54

Cys Xaa Xaa Xaa Glu Gln Arg Val Cys
1               5

<210> SEQ ID NO 55
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (5)..(7)
<223> OTHER INFORMATION: Xaa can be any naturally occurring amino acid

<400> SEQUENCE: 55

Cys Gly Arg Arg Xaa Xaa Xaa Val Cys
1               5

<210> SEQ ID NO 56
<211> LENGTH: 9
```

```
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 56

Cys Xaa Gly Arg Arg Xaa Xaa Val Cys
1               5

<210> SEQ ID NO 57
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

Cys Xaa Xaa Gly Arg Arg Xaa Val Cys
1               5

<210> SEQ ID NO 58
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(4)
<223> OTHER INFORMATION: Xaa can be any naturally occurring amino acid

<400> SEQUENCE: 58

Cys Xaa Xaa Xaa Gly Arg Arg Val Cys
1               5

<210> SEQ ID NO 59
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (6)..(7)
<223> OTHER INFORMATION: Xaa can be any naturally occurring amino acid

<400> SEQUENCE: 59

Cys Gly Gly Gly Gly Xaa Xaa Val Cys
1               5

<210> SEQ ID NO 60
<211> LENGTH: 9
<212> TYPE: PRT
<213> ORGANISM: Artificial
<220> FEATURE:
```

```
<223> OTHER INFORMATION: formula
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 60

Cys Xaa Gly Gly Gly Gly Xaa Val Cys
1               5

<210> SEQ ID NO 61
<211> LENGTH: 9
<212> TYPE: PRT
<213> ORGANISM: Artificial
<220> FEATURE:
<223> OTHER INFORMATION: formula
<220> FEATURE:
<221> NAME/KEY: misc_feature
<222> LOCATION: (2)..(3)
<223> OTHER INFORMATION: Xaa can be any naturally occurring amino acid

<400> SEQUENCE: 61

Cys Xaa Xaa Gly Gly Gly Gly Val Cys
1               5
```